United States Patent
Deschamps et al.

(10) Patent No.: US 12,065,689 B2
(45) Date of Patent: Aug. 20, 2024

(54) METHODS FOR THE IDENTIFICATION AND CHARACTERIZATION OF DOUBLE-STRAND BREAK SITES AND COMPOSITIONS AND USES THEREOF

(71) Applicants: PIONEER HI-BRED INTERNATIONAL, INC., Johnston, IA (US); VILNIUS UNIVERSITY, Vilnius (LT)

(72) Inventors: Stephane Deschamps, West Des Moines, IA (US); Virginijus Siksnys, Vilnius (LT); Joshua K Young, Johnston, IA (US); Mindaugas Zaremba, Vilnius (LT)

(73) Assignees: PIONEER HI-BRED INTERNATIONAL, INC, Johnston, IA (US); VILNIUS UNIVERSITY, Vilnius (LT)

( * ) Notice: Subject to any disclaimer, the term of this patent is extended or adjusted under 35 U.S.C. 154(b) by 636 days.

(21) Appl. No.: 17/054,637

(22) PCT Filed: May 10, 2019

(86) PCT No.: PCT/US2019/031719
§ 371 (c)(1),
(2) Date: Nov. 11, 2020

(87) PCT Pub. No.: WO2019/217816
PCT Pub. Date: Nov. 14, 2019

(65) Prior Publication Data
US 2021/0147909 A1    May 20, 2021

Related U.S. Application Data

(60) Provisional application No. 62/670,366, filed on May 11, 2018.

(51) Int. Cl.
*C12Q 1/6806* (2018.01)
*C12Q 1/6869* (2018.01)

(52) U.S. Cl.
CPC ......... *C12Q 1/6806* (2013.01); *C12Q 1/6869* (2013.01); *C12Q 2521/301* (2013.01); *C12Q 2521/525* (2013.01); *C12Q 2525/191* (2013.01); *C12Q 2535/122* (2013.01)

(58) Field of Classification Search
CPC ............... C12Q 1/6806; C12Q 1/6869; C12Q 2521/301; C12Q 2521/525; C12Q 2525/191; C12Q 2535/122; C12Q 2563/131; C12N 9/16; C12N 15/1093; C12N 9/22
See application file for complete search history.

(56) References Cited

U.S. PATENT DOCUMENTS

| | | |
|---|---|---|
| 2016/0032297 A1 | 2/2016 | Deschamps et al. |
| 2016/0340746 A1 | 11/2016 | Makarov et al. |
| 2017/0029880 A1 | 2/2017 | Fang et al. |

FOREIGN PATENT DOCUMENTS

| | | |
|---|---|---|
| WO | 2016/186946 A1 | 11/2016 |
| WO | 2018/035062 A1 | 2/2018 |

OTHER PUBLICATIONS

Shi et al., GUIDE-Seq to Detect Genome-wide Double-StrandedBreaks in plants, 2016, Trends in Plant Science, 21, pp. 815-818 ( Year: 2016).*
International Search Report and Written Opinion for PCT/US2019/31719 dated Oct. 18, 2019.

* cited by examiner

*Primary Examiner* — Narayan K Bhat
(74) *Attorney, Agent, or Firm* — Bookoff McAndrews, PLLC

(57) ABSTRACT

Methods and compositions are provided for the identification, detection, characterization, and/or utilization of double strand breaks in a target polynucleotide; the identification, detection, characterization, and/or utilization of cutting sites for double-strand-break-inducing agents; and the identification, detection, characterization, and/or utilization of double-strand-break-inducing agents.

64 Claims, 10 Drawing Sheets

Specification includes a Sequence Listing.

(to Step H, Figure 4b)

FIG. 5A

| Physical Position (B73 AGPv4) | Site ID | SEQ ID | \multicolumn{20}{c|}{Relative Nucleotide Position vs PAM sequence} |
|---|---|---|---|---|---|---|---|---|---|---|---|---|---|---|---|---|---|---|---|---|
| | | | 20 | 19 | 18 | 17 | 16 | 15 | 14 | 13 | 12 | 11 | 10 | 9 | 8 | 7 | 6 | 5 | 4 | 3 | 2 | 1 |
| Chr2:4233973-4233995 | target 1 | 16 | G | G | C | G | G | C | G | G | C | G | A | G | G | T | A | G | T | G | C | G |
| Chr1:300054908-300054930 | variant 2 | 17 | G | G | T | G | G | C | G | G | C | G | A | G | G | T | A | G | A | G | C | G |
| Chr10:109136210-109136232 | variant 3 | 18 | G | A | C | G | G | C | G | G | C | G | A | G | G | T | A | G | T | G | C | G |
| Chr10:147052395-147052417 | variant 4 | 19 | G | G | A | G | G | C | G | G | C | G | A | G | G | T | A | G | T | G | C | G |
| Chr2:158764766-158764788 | variant 5 | 20 | G | A | C | G | G | C | G | G | C | G | A | G | G | T | A | G | A | G | C | G |
| Chr7:15549845-15549867 | variant 6 | 21 | G | G | T | G | G | C | G | G | C | G | A | G | G | T | A | G | A | G | C | G |
| Chr7:65591842-65591864 | variant 7 | 22 | G | A | C | G | G | C | G | G | C | G | A | G | G | T | A | G | A | G | C | G |
| Chr1:124743265-124743287 | variant 8 | 23 | G | T | C | G | G | C | G | G | C | G | A | G | G | T | A | G | G | G | C | G |
| Chr1:124744845-124744867 | variant 9 | 24 | G | T | C | G | G | C | G | G | C | G | A | G | G | T | A | G | G | G | C | G |
| Chr10:30400620-30400642 | variant 10 | 25 | G | G | T | G | G | C | G | G | C | G | A | G | G | T | A | G | A | G | C | G |
| Chr3:193339524-193339546 | variant 11 | 26 | G | G | T | G | G | T | G | G | C | G | A | G | G | T | A | G | A | G | C | G |
| Chr3:43509499-43509521 | variant 12 | 27 | G | G | A | G | G | C | A | T | C | G | A | G | G | T | A | G | A | G | C | G |
| Chr8:174469435-174469457 | variant 13 | 28 | G | C | C | G | A | C | G | G | A | G | A | G | G | T | A | G | T | C | C | T |
| Chr8:42128283-42128305 | variant 14 | 29 | G | G | T | G | G | C | G | G | C | G | A | G | G | T | A | G | A | G | C | G |

FIG. 5B

| Physical Position (B73 AGPv4) | Site ID | | | PAM | |
|---|---|---|---|---|---|
| Chr2:4233973-4233995 | target | 1 | A | G | G |
| Chr1:300054908-300054930 | variant | 2 | T | G | G |
| Chr10:109136210-109136232 | variant | 3 | C | G | G |
| Chr10:147052395-147052417 | variant | 4 | A | G | G |
| Chr2:158764766-158764788 | variant | 5 | A | G | G |
| Chr7:15549845-15549867 | variant | 6 | T | G | G |
| Chr7:65591842-65591864 | variant | 7 | A | G | G |
| Chr1:124743265-124743287 | variant | 8 | G | G | G |
| Chr1:124744845-124744867 | variant | 9 | G | G | G |
| Chr10:30400620-30400642 | variant | 10 | T | G | G |
| Chr3:193339524-193339546 | variant | 11 | T | G | G |
| Chr3:43509499-43509521 | variant | 12 | T | G | G |
| Chr8:174469435-174469457 | variant | 13 | T | G | G |
| Chr8:42128283-42128305 | variant | 14 | T | G | G |

SEQUENCE LISTING

<160> NUMBER OF SEQ ID NOS: 32

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
```

```
                     1010                1015                1020
Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 2
<211> LENGTH: 20
<212> TYPE: DNA
<213> ORGANISM: Zea mays

<400> SEQUENCE: 2
ggcggcggcg aggtagtgcg                                                20

<210> SEQ ID NO 3
<211> LENGTH: 59
<212> TYPE: DNA
<213> ORGANISM: Artificial
<220> FEATURE:
<223> OTHER INFORMATION: Adapter 1 Forward (T overhang)

<400> SEQUENCE: 3
gttgacatgc tggattgaga cttcctacac tctttcccta cacgacgctc ttccgatct    59

<210> SEQ ID NO 4
<211> LENGTH: 59
<212> TYPE: DNA
<213> ORGANISM: Artificial
<220> FEATURE:
<223> OTHER INFORMATION: Adapter 1 Forward (A overhang)

<400> SEQUENCE: 4
gttgacatgc tggattgaga cttcctacac tctttcccta cacgacgctc ttccgatca    59

<210> SEQ ID NO 5
<211> LENGTH: 59
<212> TYPE: DNA
<213> ORGANISM: Artificial
<220> FEATURE:
<223> OTHER INFORMATION: Adapter 1 Forward (C overhang)

<400> SEQUENCE: 5
gttgacatgc tggattgaga cttcctacac tctttcccta cacgacgctc ttccgatcc    59

<210> SEQ ID NO 6
<211> LENGTH: 59
<212> TYPE: DNA
<213> ORGANISM: Artificial
<220> FEATURE:
<223> OTHER INFORMATION: Adapter 1 Forward (G overhang)

<400> SEQUENCE: 6
gttgacatgc tggattgaga cttcctacac tctttcccta cacgacgctc ttccgatcg    59

<210> SEQ ID NO 7
<211> LENGTH: 58
<212> TYPE: DNA
<213> ORGANISM: Artificial
<220> FEATURE:
<223> OTHER INFORMATION: Adapter 1 Reverse

<400> SEQUENCE: 7
gatcggaaga gcgtcgtgta gggaaagagt gtaggaagtc tcaatccagc atgtcaac     58

<210> SEQ ID NO 8
<211> LENGTH: 50
<212> TYPE: DNA
<213> ORGANISM: Artificial
<220> FEATURE:
<223> OTHER INFORMATION: Adapter 2 N7 Forward
<220> FEATURE:
<221> NAME/KEY: misc_feature
<222> LOCATION: (16)..(22)
<223> OTHER INFORMATION: n is a, c, g, or t

<400> SEQUENCE: 8
gtcgtattag tagtannnnn nnagatcgga agagcacacg tctgaactcc              50

```
<210> SEQ ID NO 9
<211> LENGTH: 49
<212> TYPE: DNA
<213> ORGANISM: Artificial
<220> FEATURE:
<223> OTHER INFORMATION: Adapter 2 N6 Forward
<220> FEATURE:
<221> NAME/KEY: misc_feature
<222> LOCATION: (16)..(21)
<223> OTHER INFORMATION: n is a, c, g, or t

<400> SEQUENCE: 9
gtcgtattag tagtannnnn nagatcggaa gagcacacgt ctgaactcc            49

<210> SEQ ID NO 10
<211> LENGTH: 48
<212> TYPE: DNA
<213> ORGANISM: Artificial
<220> FEATURE:
<223> OTHER INFORMATION: Adapter 2 N5 Forward
<220> FEATURE:
<221> NAME/KEY: misc_feature
<222> LOCATION: (16)..(20)
<223> OTHER INFORMATION: n is a, c, g, or t

<400> SEQUENCE: 10
gtcgtattag tagtannnnn agatcggaag agcacacgtc tgaactcc             48

<210> SEQ ID NO 11
<211> LENGTH: 15
<212> TYPE: DNA
<213> ORGANISM: Artificial
<220> FEATURE:
<223> OTHER INFORMATION: Adapter 2 Reverse

<400> SEQUENCE: 11
actactaata cgact                                                 15

<210> SEQ ID NO 12
<211> LENGTH: 19
<212> TYPE: DNA
<213> ORGANISM: Artificial
<220> FEATURE:
<223> OTHER INFORMATION: Recovery PCR Forward

<400> SEQUENCE: 12
ggagttcaga cgtgtgctc                                             19

<210> SEQ ID NO 13
<211> LENGTH: 24
<212> TYPE: DNA
<213> ORGANISM: Artificial
<220> FEATURE:
<223> OTHER INFORMATION: Recovery PCR Reverse

<400> SEQUENCE: 13
gttgacatgc tggattgaga cttc                                       24

<210> SEQ ID NO 14
<211> LENGTH: 58
<212> TYPE: DNA
<213> ORGANISM: Artificial
<220> FEATURE:
<223> OTHER INFORMATION: Index Forward
<220> FEATURE:
<221> NAME/KEY: misc_feature
<222> LOCATION: (30)..(37)
<223> OTHER INFORMATION: n is a, c, g, or t
```

<400> SEQUENCE: 14
aatgatacgg cgaccaccga gatctacacn nnnnnnnaca ctctttccct acacgacg    58

<210> SEQ ID NO 15
<211> LENGTH: 57
<212> TYPE: DNA
<213> ORGANISM: Artificial
<220> FEATURE:
<223> OTHER INFORMATION: Index Reverse
<220> FEATURE:
<221> NAME/KEY: misc_feature
<222> LOCATION: (27)..(34)
<223> OTHER INFORMATION: n is a, c, g, or t

<400> SEQUENCE: 15
caagcagaag acggcatacg agattannnn nnnngactgg agttcagacg tgtgctc    57

<210> SEQ ID NO 16
<211> LENGTH: 20
<212> TYPE: DNA
<213> ORGANISM: Zea mays

<400> SEQUENCE: 16
ggcggcggcg aggtagtgcg    20

<210> SEQ ID NO 17
<211> LENGTH: 20
<212> TYPE: DNA
<213> ORGANISM: Zea mays

<400> SEQUENCE: 17
ggtggcggcg aggtagagcg    20

<210> SEQ ID NO 18
<211> LENGTH: 20
<212> TYPE: DNA
<213> ORGANISM: Zea mays

<400> SEQUENCE: 18
gacggcggcg aggtagtgcg    20

<210> SEQ ID NO 19
<211> LENGTH: 20
<212> TYPE: DNA
<213> ORGANISM: Zea mays

<400> SEQUENCE: 19
ggaggcggcg aggtagtgcg    20

<210> SEQ ID NO 20
<211> LENGTH: 20
<212> TYPE: DNA
<213> ORGANISM: Zea mays

<400> SEQUENCE: 20
gacggcggcg aggtagagcg    20

<210> SEQ ID NO 21
<211> LENGTH: 20
<212> TYPE: DNA
<213> ORGANISM: Zea mays

<400> SEQUENCE: 21
ggtggcggcg aggtagagcg    20

<210> SEQ ID NO 22
<211> LENGTH: 20
<212> TYPE: DNA
<213> ORGANISM: Zea mays

<400> SEQUENCE: 22
gacggcggcg aggtagagcg					20

<210> SEQ ID NO 23
<211> LENGTH: 20
<212> TYPE: DNA
<213> ORGANISM: Zea mays

<400> SEQUENCE: 23
gtcggcggcg aggtagggcg					20

<210> SEQ ID NO 24
<211> LENGTH: 20
<212> TYPE: DNA
<213> ORGANISM: Zea mays

<400> SEQUENCE: 24
gtcggcggcg aggtagggcg					20

<210> SEQ ID NO 25
<211> LENGTH: 20
<212> TYPE: DNA
<213> ORGANISM: Zea mays

<400> SEQUENCE: 25
ggtggcggcg aggtagagcg					20

<210> SEQ ID NO 26
<211> LENGTH: 20
<212> TYPE: DNA
<213> ORGANISM: Zea mays

<400> SEQUENCE: 26
ggtggtggcg aggtagagcg					20

<210> SEQ ID NO 27
<211> LENGTH: 20
<212> TYPE: DNA
<213> ORGANISM: Zea mays

<400> SEQUENCE: 27
ggaggcatcg aggtagagcg					20

<210> SEQ ID NO 28
<211> LENGTH: 20
<212> TYPE: DNA
<213> ORGANISM: Zea mays

<400> SEQUENCE: 28
gccgacggag aggtagtcct					20

<210> SEQ ID NO 29
<211> LENGTH: 20
<212> TYPE: DNA
<213> ORGANISM: Zea mays

<400> SEQUENCE: 29

```
ggtggcggcg aggtagagcg                                              20

<210> SEQ ID NO 30
<211> LENGTH: 63
<212> TYPE: DNA
<213> ORGANISM: Artificial
<220> FEATURE:
<223> OTHER INFORMATION: upper strand adapter

<400> SEQUENCE: 30
agttacgcaa ccgagacgcg gccgcsgsts gsactggagt tcagacgtgt gctcttccga   60
tct                                                                63

<210> SEQ ID NO 31
<211> LENGTH: 56
<212> TYPE: DNA
<213> ORGANISM: Artificial
<220> FEATURE:
<223> OTHER INFORMATION: bottom strand adapter

<400> SEQUENCE: 31
agatcggaag agcacacgtc tgaactccag tcacgcccgg gcgtctcggt tgcddc       56

<210> SEQ ID NO 32
<211> LENGTH: 36
<212> TYPE: DNA
<213> ORGANISM: Artificial
<220> FEATURE:
<223> OTHER INFORMATION: second strand synthesis primer
<220> FEATURE:
<221> NAME/KEY: misc_feature
<222> LOCATION: (25)..(36)
<223> OTHER INFORMATION: n is a, c, g, or t

<400> SEQUENCE: 32
ccctacacga cgctcttccg atctnnnnnn nnnnnn                             36
```

METHODS FOR THE IDENTIFICATION AND CHARACTERIZATION OF DOUBLE-STRAND BREAK SITES AND COMPOSITIONS AND USES THEREOF

CROSS-REFERENCE TO RELATED APPLICATIONS

This application is a 371 National Stage Entry of PCT Application No. PCT/US2019/031719 filed on 10 May 2019, which claims the benefit of U.S. Provisional Patent Application Ser. No. 62/670,366 filed 11 May 2018, all of which are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named RTS21920AUSPCT_SeqListing_ST25.TXT created on 27 Oct. 2020 and having a size of 17,949 bytes and is filed concurrently with the specification. The sequence listing comprised in this ASCII formatted document is part of the specification and is herein incorporated by reference in its entirety.

FIELD OF THE INVENTION

This invention is in the field of molecular biology. More specifically, this invention pertains to methods for identifying, characterizing, and using recognition sites in a polynucleotide molecule for double-strand-break-inducing agents.

BACKGROUND

Advances in molecular biology have made it possible to create double-strand breaks (DSBs) in polynucleotide molecules, which may be utilized to effect the insertion, deletion, substitution, or modification of one or more nucleotides, and can involve site-specific techniques which rely on double-strand-break-inducing agents ("DSB agents") such as, but not limited to, meganucleases, zinc finger nucleases, TALENs, Argonautes, and CRISPR-Cas endonucleases.

While these systems have provided useful techniques for nucleotide modifications and targeted insertion of other polynucleotide sequences of interest, there remains a need for identifying and characterizing recognition sites for double-strand-break-inducing agents, and for identifying recognition sites with increased activity towards double-strand-break-inducing agents, including both target and off-target double-strand breaks. In particular, there is a need for methods that provide increased sensitivity for detection of double-strand breaks created by double-strand-break-inducing agents, over the detection of randomly cleaved polynucleotide fragments.

SUMMARY OF INVENTION

The invention provides compositions and methods for the detection, identification, characterization, and utilization of double-strand break sites in a polynucleotide, including those in in vitro and in vivo environments, as well as the detection, identification, characterization, and utilization of double-strand-break-inducing agents creating double-strand breaks in a polynucleotide. In some embodiments, the double-strand-break-inducing agent cleaves the target polynucleotide such that a blunt-end cut is created. In some embodiments, the double-strand-break-inducing agent cleaves the target polynucleotide such that a sticky-end cut is created. It is understood that variations of the embodiments are possible and that the methods described herein may be used for detection, identification, characterization, and utilization of either or both sticky-end or blunt-end cuts in a target polynucleotide.

In some aspects, a method is provided for characterizing a double-strand-break-inducing agent cleavage site of an isolated, purified polynucleotide, comprising: (a) adding phosphatase to the isolated, purified polynucleotide, (b) contacting the phosphatase-treated polynucleotide from (a) with a double-strand-break-inducing agent to create a library of polynucleotides, (c) optionally adding an adenine to the 3' ends of the polynucleotides of the library, and (d) ligating an adapter to the polynucleotides of the library, wherein the adapter comprises a nucleotide that is complementary to a terminal unpaired nucleotide of the polynucleotides of (b) or (c); further comprising sequencing said library of polynucleotides, identifying at least one double-strand-break site, and assessing at least one qualitative characteristic or quantitative characteristic. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus*, *B. rapa*, *B. juncea*), rice (*Oryza sativa*), wheat (*Triticum aestivum*), soybean (*Glycine max*), tobacco (*Nicotiana tabacum*), cotton (*Gossypium barbadense*, *Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site of an isolated, purified polynucleotide, comprising: (a) adding phosphatase to the isolated, purified polynucleotide, (b) contacting the phosphatase-treated polynucleotide from (a) with a double-strand-break-inducing agent to create a first library of polynucleotides with blunt ends, (c) adding an adenine to the 3' ends of the polynucleotides of the first library to create a second library of polynucleotides, (d) ligating a first adapter to the polynucleotides of the second library to create a third library of polynucleotides, wherein said first adapter comprises a molecule for the purification of the polynucleotide and a thymine complementary to the adenine added in (c), (e) fragmenting or shearing the polynucleotides of the third library of polynucleotides to create a fourth library of polynucleotides, (f) repairing the ends of, and adding a 3' adenine to, the polynucleotides of the fourth library to create a fifth library of polynucleotides, (g) ligating a second adapter to the polynucleotides of the fifth library to create a sixth library of polynucleotides, wherein said second adapter comprises a molecule to allow the amplification and sequencing of the polynucleotides, (h) capturing the first- and second-adapter ligated polynucleotides of the sixth library, (i) amplifying the polynucleotides of the sixth library, (j) sequencing the polynucleotides of the sixth library, (k) identifying at least one double-strand-break site, and (l) assessing at least one qualitative or quantitative characteristic of said double-strand-break site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, Xenopus egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a non-coding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site of an isolated, purified polynucleotide, comprising: (a) adding phosphatase to the isolated, purified polynucleotide, (b)

contacting the phosphatase-treated polynucleotide from (a) with a double-strand-break-inducing agent to create a first library of polynucleotides with sticky ends comprising at least one nucleotide overhang, (c) ligating a first adapter to the polynucleotides of the first library to create a second library of polynucleotides, wherein said first adapter comprises a molecule for the purification of the polynucleotide and a nucleotide complementary to the sticky end at least one nucleotide overhang of the polynucleotide of the first library, (d) fragmenting or shearing the polynucleotides of the second library of polynucleotides to create a third library of polynucleotides, (e) repairing the ends of, and adding a 3' adenine to, the fragments of the third library to create a fourth library of polynucleotides, (f) ligating a second adapter to the polynucleotides of the fourth library to create a fifth library of polynucleotides, wherein said second adapter comprises a molecule to allow the amplification and sequencing of the polynucleotides, (g) capturing the first- and second-adapter ligated polynucleotides of the sixth library, (h) amplifying the polynucleotides of the sixth library, (i) sequencing the polynucleotides of the sixth library, (j) identifying at least one double-strand-break site, and (k) assessing at least one qualitative or quantitative characteristic of said double-strand-break site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site, comprising: (a) adding phosphatase to a sample of isolated, purified polynucleotide, (b) contacting the phosphatase-treated polynucleotide from (a) with the double-strand-break-inducing agent to create a first library of polynucleotides, (c) repairing the ends of the polynucleotides of the first library to create a second library of polynucleotides with blunt ends, (d) adding an adenine to the 3' ends of the polynucleotides of the second library to create a third library of polynucleotides, (e) ligating a first adapter to the polynucleotides of the third library to create a fourth library of polynucleotides, wherein said first adapter comprises a molecule for the purification of the polynucleotide and a thymine complementary to the adenine added in (d), (f) fragmenting or shearing the polynucleotides of the fourth library of polynucleotides to create a fifth library of polynucleotides, (g) repairing the ends of, and adding a 3' adenine to, the polynucleotides of the fifth library to create a sixth library of polynucleotides, (h) ligating a second adapter to the polynucleotides of the sixth library to create a seventh library of polynucleotides, wherein said second adapter comprises a molecule to allow the amplification and sequencing of the polynucleotides, (i) capturing the first- and second-adapter ligated polynucleotides of the seventh library, (j) amplifying the polynucleotides of the seventh library, (k) sequencing the polynucleotides of the seventh library, (l) identifying at least one double-strand-break site, and (m) assessing at least one qualitative or quantitative characteristic of said double-strand-break-inducing site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site, comprising: (a) adding phosphatase to a sample of isolated, purified polynucleotide, (b) contacting the phosphatase-treated polynucleotide from (a) with the double-strand-break-inducing agent to create a first library of polynucleotides, (c) optionally adding an adenine to the 3' ends of the polynucleotides of the first library to create a second library of polynucleotides, (d) ligating a first adapter to the polynucleotides of the second library to create a third library of polynucleotides, wherein said first adapter comprises a molecule for the purification of the polynucleotide and a thymine complementary to the adenine added in (c), (e) fragmenting or shearing the polynucleotides of the third library of polynucleotides to create a fourth library of polynucleotides, (g) repairing the ends of, and adding a 3' adenine to, the polynucleotides of the fourth library to create a fifth library of polynucleotides, (h) ligating a second adapter to the polynucleotides of the fifth library to create a sixth library of polynucleotides, wherein said second adapter comprises a molecule to allow the amplification and sequencing of the polynucleotides, (i) capturing the first- and second-adapter ligated polynucleotides of the sixth library, (j) amplifying the polynucleotides of the sixth library, (k) sequencing the polynucleotides of the sixth library, (l) identifying at least one double-strand-break site, and (m) assessing at least one qualitative or quantitative characteristic of said double-strand-break-inducing site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site, comprising: (a) adding phosphatase to a sample of isolated, purified polynucleotide, (b) contacting the phosphatase-treated polynucleotide from (a) with the double-strand-break-inducing agent to create a first library of polynucleotides, (c) ligating a double-stranded first adapter to the polynucleotides of the first library to create a second library of polynucleotides, wherein one strand of said double-stranded first adapter comprises a molecule for the purification of the polynucleotide, (d) removing the nicks and reconstituting a restriction endonuclease site to create a third library of polynucleotides, (e) shearing the polynucleotides of the third library to create a fourth library of fragmented polynucleotides, (f) capturing the fragmented polynucleotides of the fourth library that comprise the ligated first adapter, (g) cleaving the captured fragmented polynucleotides with a restriction endonuclease capable of recognizing the site introduced in (d) to create a fifth library of polynucleotides, (h) adding lambda exonuclease to the polynucleotides of the fifth library and to create a sixth library of single stranded polynucleotides, (i) synthesizing complementary strands to the single stranded polynucleotides of the sixth library to create a seventh library, (j) purifying, amplifying, and size-selecting the polynucleotides of the seventh library, (k) sequencing the polynucleotides of the seventh library, (l) identifying at least one double-strand-break site, and (m) assessing at least one qualitative or quantitative characteristic of said double-strand-break-inducing site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site, comprising: (a) adding phosphatase to a sample of isolated, purified polynucleotide, (b) contacting the phosphatase-treated polynucleotide from (a) with the double-strand-break-inducing agent to create a first library of polynucleotides with a sticky-end cut comprising at least one nucleotide overhang, (c) ligating a double-stranded first adapter to the polynucleotides of the first library to create a second library of polynucleotides, wherein one strand of said double-stranded first adapter comprises a molecule for the purification of the polynucleotide, (d) removing the nicks and reconstituting a restriction endonuclease site to create a third library of polynucleotides, (e) shearing the polynucleotides of the third library to create a fourth library of fragmented polynucleotides, (f) capturing the fragmented polynucleotides of the fourth library that comprise the ligated first adapter, (g) cleaving the captured fragmented polynucleotides with a restriction endonuclease capable of recognizing the site introduced in (d) to create a fifth library of polynucleotides, (h) adding lambda exonuclease to the polynucleotides of the fifth library and to create a sixth library of single stranded polynucleotides, (i) synthesizing complementary strands to the single stranded polynucleotides of the sixth library to create a seventh library, (j) purifying, amplifying, and size-selecting the polynucleotides of the seventh library, (k) sequencing the polynucleotides of the seventh library, (l) identifying at least one double-strand-break site, and (m) assessing at least one qualitative or quantitative characteristic of said double-strand-break-inducing site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, a method is provided for characterizing a double-strand-break-inducing agent cleavage site, comprising: (a) adding phosphatase to a sample of isolated, purified polynucleotide, (b) contacting the phosphatase-treated polynucleotide from (a) with the double-strand-break-inducing agent to create a first library of polynucleotides with a blunt-end cut, (c) ligating a double-stranded first adapter to the polynucleotides of the first library to create a second library of polynucleotides, wherein one strand of said double-stranded first adapter comprises a molecule for the purification of the polynucleotide, (d) removing the nicks and reconstituting a restriction endonuclease site to create a third library of polynucleotides, (e) shearing the polynucleotides of the third library to create a fourth library of fragmented polynucleotides, (f) capturing the fragmented polynucleotides of the fourth library that comprise the ligated first adapter, (g) cleaving the captured fragmented polynucleotides with a restriction endonuclease capable of recognizing the site introduced in (d) to create a fifth library of polynucleotides, (h) adding lambda exonuclease to the polynucleotides of the fifth library and to create a sixth library of single stranded polynucleotides, (i) synthesizing complementary strands to the single stranded polynucleotides of the sixth library to create a seventh library, (j) purifying, amplifying, and size-selecting the polynucleotides of the seventh library, (k) sequencing the polynucleotides of the seventh library, (l) identifying at least one double-strand-break site, and (m) assessing at least one qualitative or quantitative characteristic of said double-strand-break-inducing site. In some embodiments, the sequences of the polynucleotides of the last library are compared to the sequence(s) of at least one reference polynucleotide or genome. In some embodiments, the polynucleotide is selected from the group consisting of: cDNA, plasmid DNA, genomic DNA, and synthetic DNA. In some embodiments, the polynucleotide is linear. In some embodiments, the polynucleotide is circularized. In some embodiments, the first adapter is non-phosphorylated. In some embodiments, the polynucleotide is obtained from a cell. In some embodiments, the cell is a prokaryotic cell or a eukaryotic cell. In some embodiments, the cell is transgenic. In some embodiments, the eukaryotic cell is selected from the group consisting of: animal, plant, and fungus. In some embodiments, the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell. In some embodiments, the plant cell is selected from the group consisting of: *Arabidposis*, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp. In some embodiments, the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain. In some embodiments, the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding. In some embodiments, the polynucleotide library generated in the fragmenting/shearing step comprises polynucleotide molecules between 100 and 1000 nucleotides in length, between 10 and 100 nucleotides in length, or between 1 and 100 nucleotides in length. In some embodiments, the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. In some embodiments, any of the polynucleotide compositions comprise a polynucleotide of interest selected from the group consisting of: a Protospacer Adjacent Motif (PAM) sequence, a double-strand-break-inducing agent polynucleotide sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide. In some embodiments, a characteristic of the double-strand-break-inducing agent is additionally determined. In some embodiments, the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent. In some embodiments, a value of a characteristic is compared to the value of the same characteristic of, or produced by, a reference double-strand-break-inducing agent. In some embodiments, a value of a characteristic is increased as compared to that of a reference. In some embodiments, a value of a characteristic is decreased as compared to that of a reference. In some embodiments, a value of a characteristic is increased as the same as that of a reference. In some embodiments, a value of a characteristic is used to optimize a characteristic of a double-strand-break-inducing agent functional association. In some embodiments, the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex. In some embodiments, the cleavage site is a target cleavage site. In some embodiments, the cleavage site is an off-target cleavage site. In some embodiments, the double-strand-break-inducing agent of step (b) comprises a ribonucleoprotein comprising a Cas endonuclease and a guide ribonucleotide. In some embodiments, the double-strand-break-inducing agent of step (b) comprises a ribonucleoprotein comprising a Cas endonuclease and a guide ribonucleotide, and the concentration of the ribonucleoprotein is at least 0.05 nM, at least 0.10 nM, at least 0.25 nM, at least 0.50 nM, at least 0.75 nM, or greater than 0.75 nM. In some embodiments, the double-strand-break-inducing agent of step (b) comprises a ribonucleoprotein comprising a Cas endonuclease and a guide ribonucleotide, and the ratio of guide RNA to Cas endonuclease is 1:1, 2:1, 3:1, 4:1, 5:1, or greater than 5:1. In some embodiments, the double-strand-break-inducing agent of step (b) comprises a ribonucleoprotein comprising a Cas endonuclease and a guide ribonucleotide, and the ratio of Cas endonuclease to guide RNA is 1:1, 2:1, 3:1, 4:1, 5:1, or greater than 5:1. In some embodiments, a plurality of double-strand-break-inducing agents are evaluated in parallel. In some embodiments, a plurality of double-strand-break-inducing agents are evaluated in sequence.

In some aspects, the method according to FIG. 1 is provided.

In some aspects, the method according to FIG. 2 is provided.

In some aspects, the method according to FIG. 3 is provided.

In some aspects, the method according to FIG. 4 is provided.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821 and 1.825.

Figure 3:
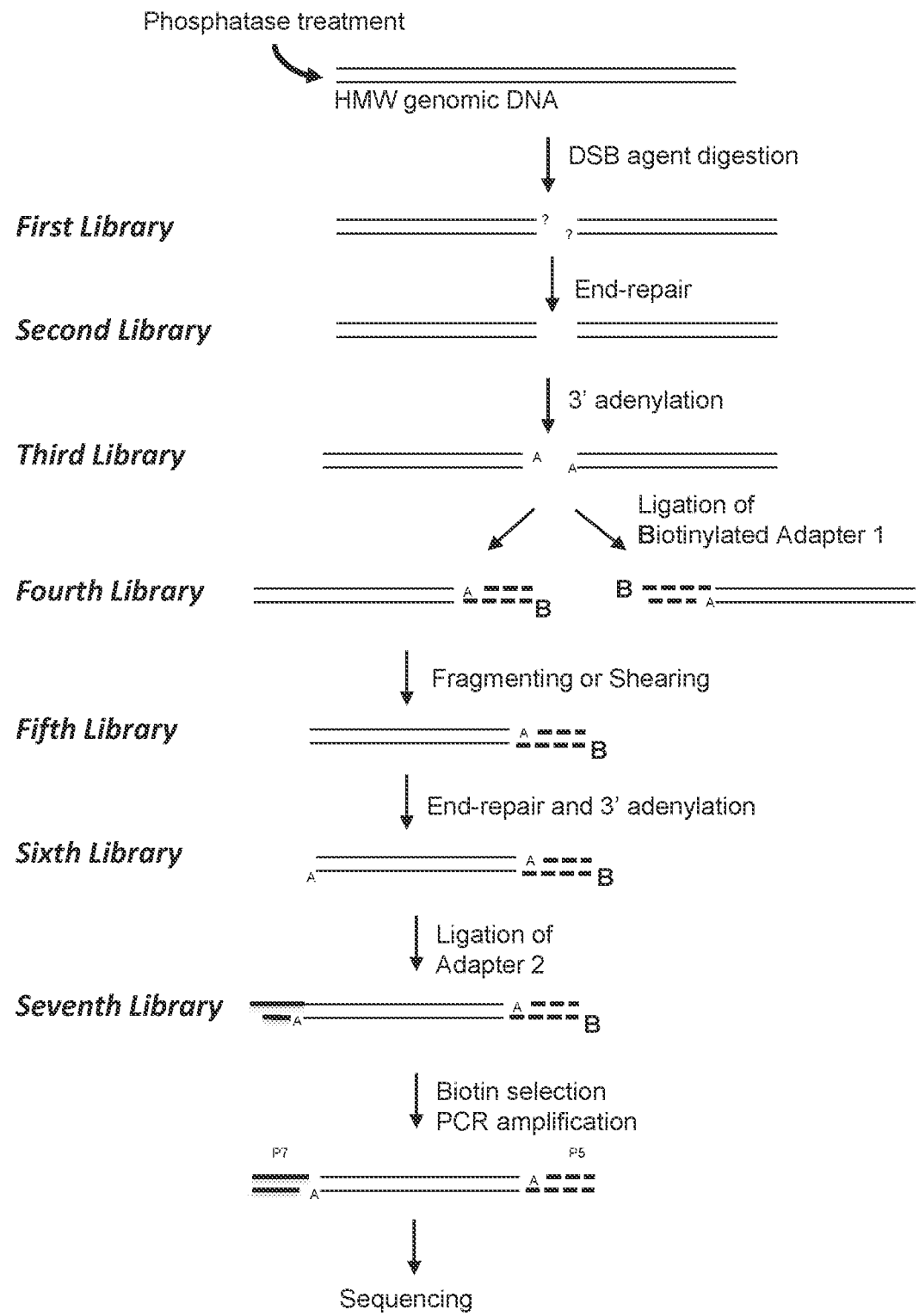
FIG. 3 depicts one embodiment of the disclosed method, for the identification and characterization of a double-strand break produced by a double-strand-break-inducing agent, wherein the nature of the cleavage (e.g., blunt-end or sticky-end) is either not known, or the activity of the DSB agent is mixed or incomplete.
Figure 4A:
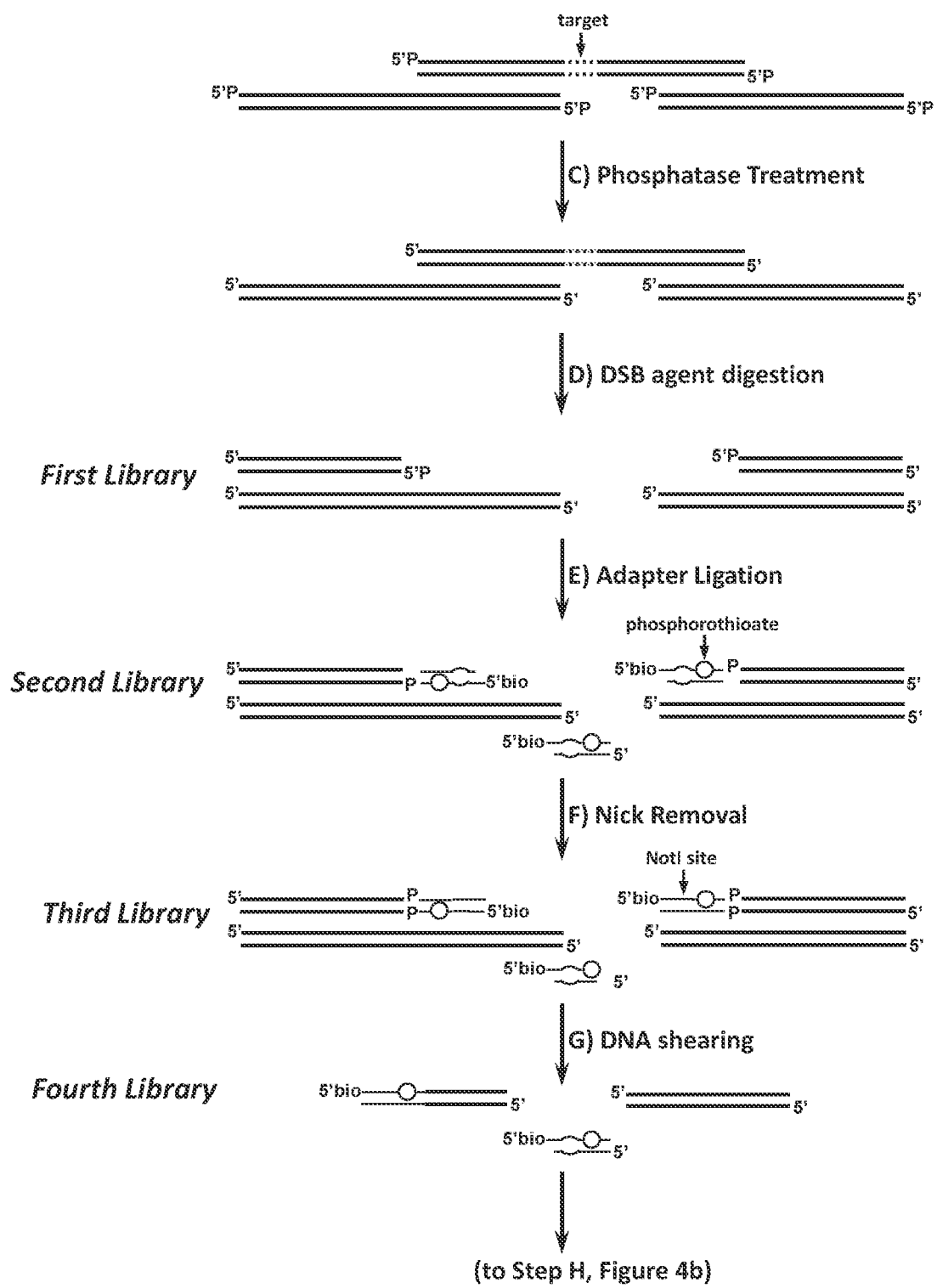
Figure 4B:
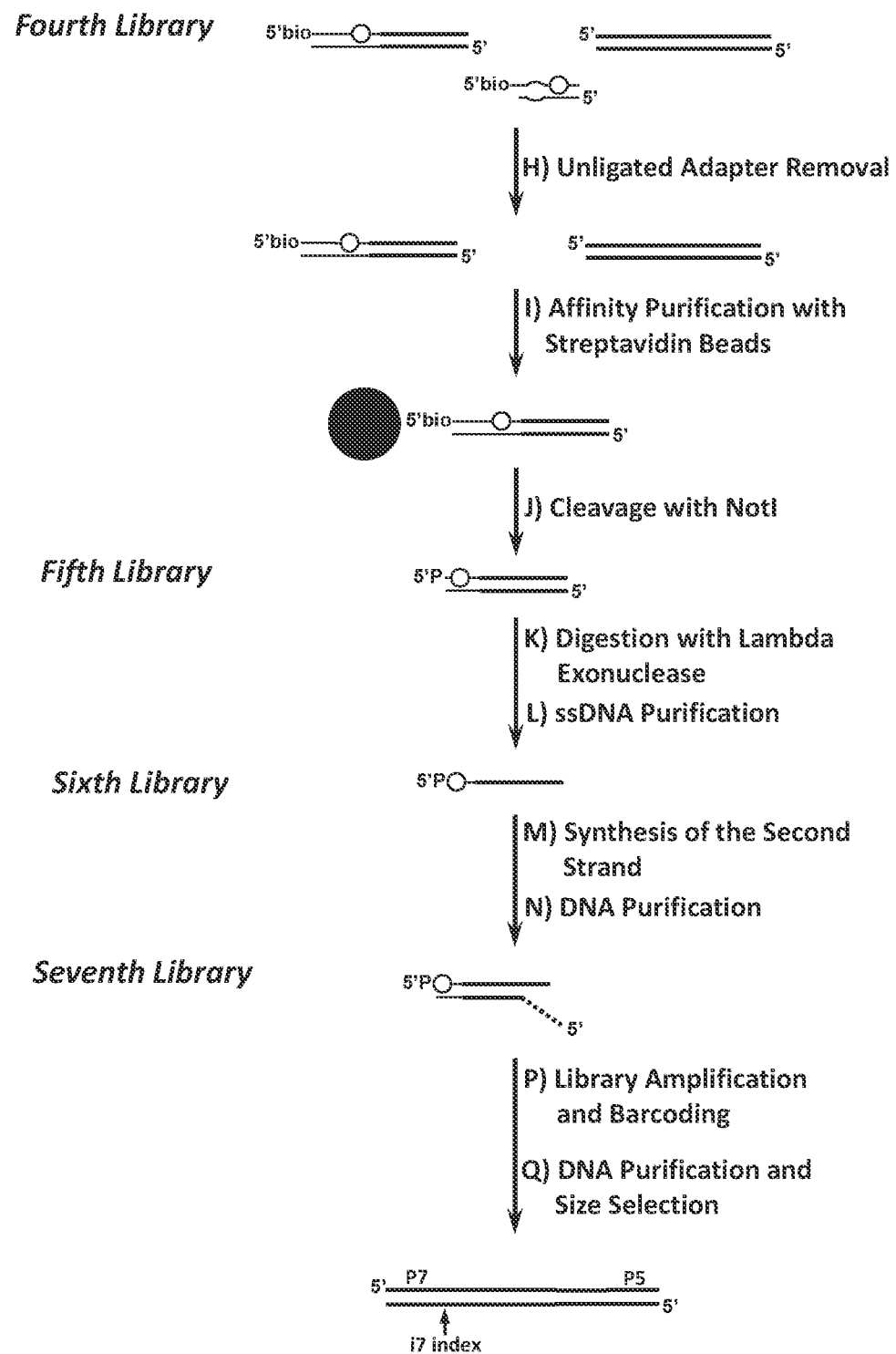

FIG. 4 depicts one embodiment of the disclosed method (as described in Example 16), for the identification and characterization of a double-strand break produced by a double-strand-break-inducing agent capable of effecting a "blunt-end" cut in a double-stranded polynucleotide. FIG. 4A depicts the first part of the method and FIG. 4B depicts the last part of the method. Additional variations of this method may be adapted for "sticky-end" cuts, when the nature of the cleavage is not known, or the activity of the DSB agent is mixed or incomplete, similar to the variations of FIG. 1 described in FIGS. 2 and 3.

FIG. 5A shows the target and off-target recognition sequences identified in the maize B73 genome in experiments using the S. pyogenes Cas9-M19 gRNA RNP complex. Fourteen of the recognition and cleavage sites were detected (1 target and 13 off-target). The double-strand-break was induced between the third and fourth nucleotides downstream of the PAM sequence (nucleotides are numbered relative to the PAM sequence). Any nucleotide variation in a off-target recognition site, as compared to the nucleotide(s) of the target recognition site, are highlighted with bold lines around the respective nucleotide(s). FIG. 5B shows the PAM sequences for each of the target and 13 off-target recognition sites in the maize B73 genome in experiments using the S. pyogenes Cas9-M19 gRNA RNP complex.

Figure 6:
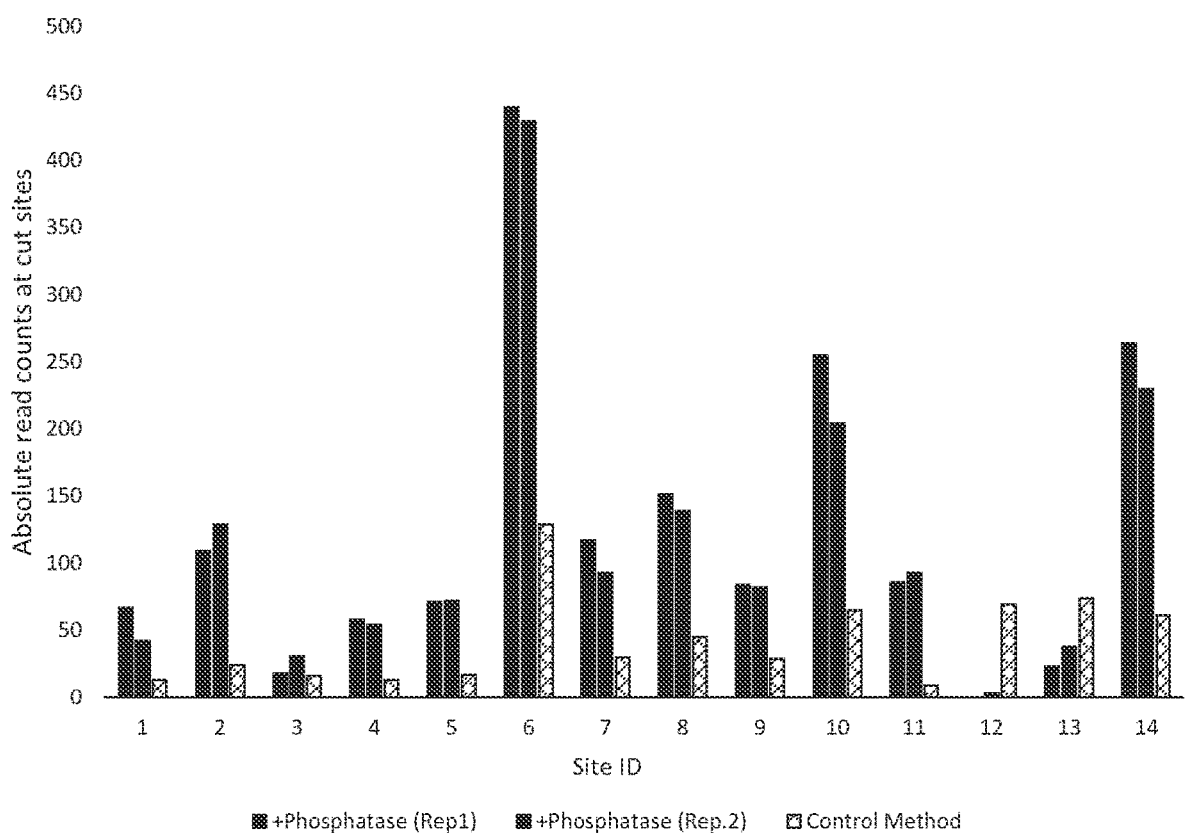

FIG. 6 graphically depicts the results of treating purified genomic DNA from leaf cells of plants from the maize B73 with the *S. pyogenes* Cas9-M19 gRNA RNP complex, which generated at least fourteen double-strand break sites. Two replications of treatment with phosphatase prior to polynucleotide fragmentation were compared to one treatment with no phosphatase prior to fragmentation.

Figure 7:
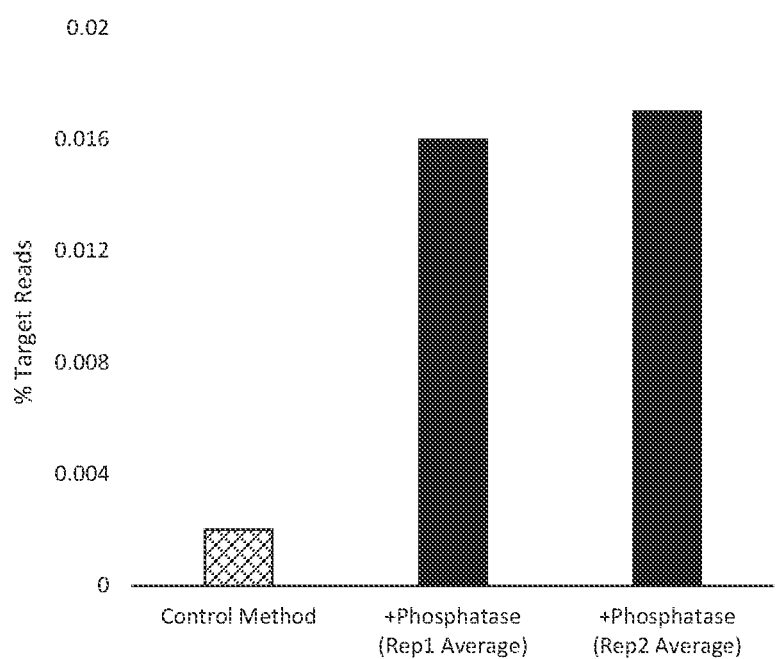

FIG. 7 shows the average percent reads (target and off-target) of the two replications of phosphatase treatment method, compared to the results of genomic DNA without phosphatase treatment.

Figure 8:
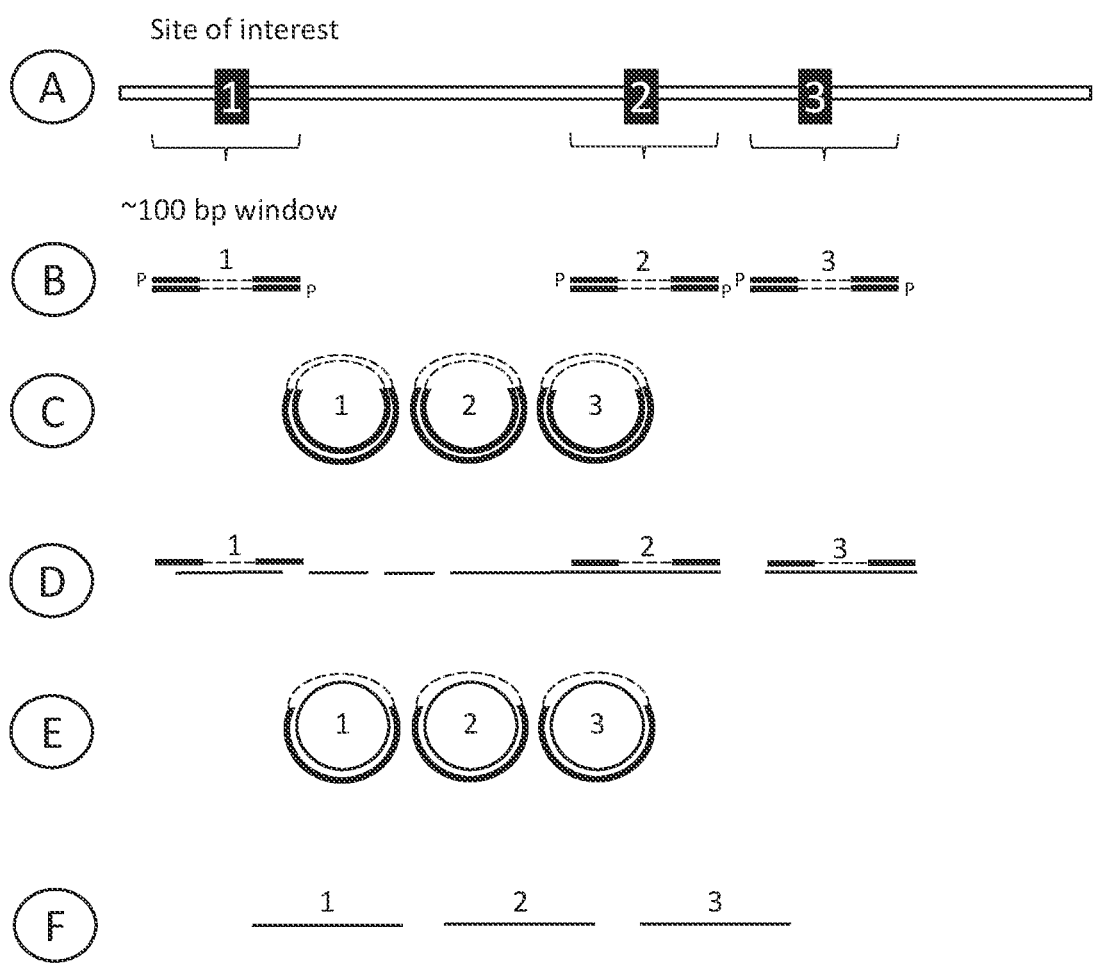

FIG. 8 depicts the Molecular Inversion Probes Sequencing (MIPs) method of Example 17.

SEQ ID NO:1 is the Cas9 protein PRT sequence from *Streptococcus pyogenes*.

SEQ ID NO:2 is the sgRNA DNA sequence from *Zea mays*.

SEQ ID NO:3 is the Adapter 1 Forward (T overhang) DNA sequence.

SEQ ID NO:4 is the Adapter 1 Forward (A overhang) DNA sequence.

SEQ ID NO:5 is the Adapter 1 Forward (C overhang) DNA sequence.

SEQ ID NO:6 is the Adapter 1 Forward (G overhang) DNA sequence.

SEQ ID NO:7 is the Adapter 1 Reverse DNA sequence.

SEQ ID NO:8 is the Adapter 2 N7 Forward DNA sequence.

SEQ ID NO:9 is the Adapter 2 N6 Forward DNA sequence.

SEQ ID NO:10 is the Adapter 2 N5 Forward DNA sequence.

SEQ ID NO:11 is the Adapter 2 Reverse DNA sequence.

SEQ ID NO:12 is the Recovery PCR Forward DNA sequence.

SEQ ID NO:13 is the Recovery PCR Reverse DNA sequence.

SEQ ID NO:14 is the Index Forward DNA sequence.

SEQ ID NO:15 is the Index Reverse DNA sequence.

SEQ ID NO:16 is the Target Site 1 DNA sequence from *Zea mays*.

SEQ ID NO:17 is the Variant Site 2 DNA sequence from *Zea mays*.

SEQ ID NO:18 is the Variant Site 3 DNA sequence from *Zea mays*.

SEQ ID NO:19 is the Variant Site 4 DNA sequence from *Zea mays*.

SEQ ID NO:20 is the Variant Site 5 DNA sequence from *Zea mays*.

SEQ ID NO:21 is the Variant Site 6 DNA sequence from *Zea mays*.

SEQ ID NO:22 is the Variant Site 7 DNA sequence from *Zea mays*.

SEQ ID NO:23 is the Variant Site 8 DNA sequence from *Zea mays*.

SEQ ID NO:24 is the Variant Site 9 DNA sequence from *Zea mays*.

SEQ ID NO:25 is the Variant Site 10 DNA sequence from *Zea mays*.

SEQ ID NO:26 is the Variant Site 11 DNA sequence from *Zea mays*.

SEQ ID NO:27 is the Variant Site 12 DNA sequence from *Zea mays*.

SEQ ID NO:28 is the Variant Site 13 DNA sequence from *Zea mays*.

SEQ ID NO:29 is the Variant Site 14 DNA sequence from *Zea mays*.

SEQ ID NO:30 is the upper strand adapter DNA sequence. Modifications are indicated as follows: 5'-Biotin-AGTTACGCAACCGAGACGCGGCCGCsGsTsGsACTG-GAGTTCAGACGTGTGCTCTTCC GATCT-3', where "s" stands for PTO modification.

SEQ ID NO:31 is the bottom strand adapter DNA sequence. Modifications are indicated as follows: 5'-AG-ATCGGAAGAGCACACGTCTGAACTCCAGT-CACGCCCGGGCGTCTCGGTTGCddC-3'

SEQ ID NO:32 is the Second strand synthesis primer DNA sequence.

DETAILED DESCRIPTION

Methods and compositions are provided for the identification and characterization of double-strand-break-inducing agent recognition sites in a polynucleotide.

Terms used in the claims and specification are defined as set forth below unless otherwise specified. It must be noted that, as used in the specification and the appended claims, the singular forms "a," "an" and "the" include plural referents unless the context clearly dictates otherwise.

Definitions

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

As used herein, the terms "target site", "target sequence", "genomic target site" and "genomic target sequence" are used interchangeably herein and refer to a polynucleotide sequence in the genome of a plant cell, animal cell, bacterial cell, or yeast cell that comprises a recognition site for a double-strand-break-inducing agent.

An "artificial target site" is a target sequence that has been introduced into the genome of an organism such as a plant, animal, or yeast. Such an artificial target sequence can be identical in sequence to an endogenous or native target sequence in the genome of the organism but can be located in a different position (i.e., a non-endogenous or non-native position) in the genome of the organism.

The terms "endogenous target sequence" and "native target sequence" are used interchangeable herein to refer to a target sequence that is endogenous or native to the genome of a host (such as a plant, animal, or yeast) and is at the endogenous or native position of that target sequence in the genome of the host (such as a plant, animal, or yeast).

A "break-inducing agent" is a composition that creates a cleavage in at least one strand of a polynucleotide. In some aspect, a break-inducing agent may be capable of, or have its activity altered such that it is capable of, creating a break in only one strand of a polynucleotide. Producing a single-strand-break in a double-stranded target sequence may be referred to herein as "nicking" the target sequence.

The term "double-strand-break-inducing agent", or equivalently "double-strand-break agent" or "DSB agent", as used herein refers to any composition which produces a double-strand break in a target polynucleotide sequence; that is, creates a break in both strands of a double stranded polynucleotide. Examples of a DSB agent include, but are not limited to: meganucleases, TAL effector nucleases, Argonautes, Zinc Finger nucleases, and Cas endonucleases (either individually or as part of a ribonucleoprotein complex). Producing the double-strand break in a target sequence may be referred to herein as "cutting" or "cleaving" the target sequence. In some aspects, the DSB agent is a nuclease. In some aspects, the DSB agent is an endonuclease. An "endonuclease" refers to an enzyme that cleaves the phosphodiester bond within a polynucleotide chain. In some embodiments, the double-strand break results in a "blunt" end of a double-stranded polynucleotide, wherein both strands are cut directly across from each other with no nucleotide overhang generated. A "blunt" end cut of a double-stranded polynucleotide is created when a first cleavage of the first stand polynucleotide backbone occurs between a first set of two nucleotides on one strand, and a second cleavage of the second strand polynucleotide backbone occurs between a second set of two nucleotides on the opposite strand, wherein each of the two nucleotides of the first set are hydrogen bonded to one of the two nucleotides of the second set, resulting in cut strands with no nucleotide on the cleaved end that is not hydrogen bonded to another nucleotide on the opposite strand. In some embodiments, the double-strand break results in a "sticky" end of a double-stranded polynucleotide, wherein cuts are made between nucleotides of dissimilar relative positions on each of the two strands, resulting in a polynucleotide overhang of one strand compared to the other. A "sticky" end cut of a double-stranded polynucleotide is created when a first cleavage of the first strand polynucleotide backbone occurs between a first set of two nucleotides on one strand, and a second cleavage of the second strand polynucleotide backbone occurs between a second set of two nucleotides on the opposite strand, wherein no more than one nucleotide of the first set is hydrogen bonded to one of the nucleotides of the second set on the opposite strand, resulting in an "overhang" of at least one polynucleotide on one of the two strands wherein the lengths of the two resulting cut strands are not identical. In some embodiments, the DSB agent comprises more than one type of molecule. In one non-limiting example, the DSB agent comprises an endonuclease protein and a polynucleotide, for example a Cas endonuclease and a guide RNA. In some aspects, the DSB agent is a fusion protein comprising a plurality of polypeptides. In one non-limiting example, the DSB agent is a Cas endonuclease with a deactivated nuclease domain, and another polypeptide with nuclease activity.

As used herein, the term "recognition site" refers to a polynucleotide sequence to which a double-strand-break-inducing agent is capable of alignment, and may optionally contact, bind, and/or effect a double-strand break. The terms "recognition site" and "recognition sequence" are used interchangeably herein. The recognition site can be an endogenous site in a host (such as a yeast, animal, or plant) genome, or alternatively, the recognition site can be heterologous to the host (yeast, animal, or plant) and thereby not be naturally occurring in the genome, or the recognition site can be found in a heterologous genomic location compared to where it occurs in nature. The length and the composition of a recognition site can be characteristic of, and may be specific to, a particular double-strand-break-inducing agent. The cleavage site of a DSB agent may be the same or different than the recognition site, and may be the same or different than the binding site.

As used herein, the term "endogenous recognition (or binding or cleavage) site" refers to a double-strand-break-inducing agent recognition (or binding or cleavage) site that is endogenous or native to the genome of a host (such as a plant, animal, or yeast) and is located at the endogenous or native position of that recognition (or binding or cleavage) site in the genome of the host (such as a plant, animal, or yeast). The length of the recognition (or binding or cleavage) site can vary, and includes, for example, recognition (or binding or cleavage) sites that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or more than 70 nucleotides in length. The composition of the recognition (or binding or cleavage) site can vary, and includes, for example, a plurality of specific nucleotides whose compositions are recognized by the DSB agent. In some aspects, the plurality of specific nucleotides is contiguous in the primary sequence. In some aspects, the plurality of specific nucleotides is non-contiguous in the primary sequence. It is further possible that the recognition site could be palindromic, that is, the sequence on one strand reads the same in the opposite direction on the complementary strand. The binding and/or nick/cleavage site could be within the recognition sequence or the binding and/or nick/cleavage site could be outside of the recognition sequence. In another variation, the DSB cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

As used herein, the term "target recognition site" refers to the polynucleotide sequence to which a double-strand-break-inducing agent is capable of aligning perfectly (i.e., zero nucleotide mismatches, gaps, or insertions), and in some aspects, induces a double-strand break.

As used herein, the term "off-target recognition site" refers to a polynucleotide sequence to which a double-strand-break-inducing agent is incapable of perfect alignment but is capable of imperfect alignment, and in some aspects, binds to and/or induces a double-strand break. An "off-target recognition site" comprises at least one base nucleotide alteration when compared to the target recognition site.

As used herein, the term "target binding site" refers to the polynucleotide sequence at which the double-strand-break-inducing agent is capable of forming a functional association, and to which it forms bonds with complementary nucleotides of the target polynucleotide strand, with perfect alignment (i.e., zero nucleotide mismatches, gaps, or insertions).

As used herein, the term "off-target binding site" refers to a polynucleotide sequence that comprises at least one nucleotide alteration when compared to the target binding site.

As used herein, the term "target cleavage site" refers to the polynucleotide sequence at which a double-strand-break-inducing agent is capable of producing a double-strand break, with perfect alignment (i.e., zero nucleotide mismatches, gaps, or insertions).

As used herein, the term "off-target cleavage site" refers to a polynucleotide sequence that comprises at least one base nucleotide alteration when compared to the target cleavage site.

The "at least one base nucleotide alteration" may include, for example: (i) replacement of at least one nucleotide, (ii) a deletion of at least one nucleotide, (iii) an insertion of at least one nucleotide, (iv) modification of at least one nucleotide, or (v) any combination of (i)-(iv). Functional variants and fragments of the recognition can share at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to the given recognition sequence, wherein the functional variant or functional fragment retains biological activity and hence are capable of being recognized and cleaved by an endonuclease. An off-target recognition site, off-target binding site, or off-target cleavage site can comprise at least one (1) and up to 2, 3, 5, 6, 7, 8, 9, 10, 11, 12, 13, 14, 15, 16, 17, 18, 19 or 20 off-nucleotide preferences, as compared to the target recognition site, target binding site, or target cleavage site, respectively. In one embodiment, an off-target recognition site, off-target binding site, or off-target cleavage site is non-endogenous to the host genome. In another embodiment, an off-target recognition site, off-target binding site, or off-target cleavage site is present in the host genome (referred to as genomic off-target recognition site, genomic off-target binding site, or genomic off-target cleavage site) or endogenous to the host genome, such as plant, animal, or yeast genomes. In some embodiments, an off-target recognition site, off-target binding site, or off-target cleavage site can be introduced into a plant genome by the mutagenesis of an endogenous genomic sequence. Methods for the site-specific mutagenesis of genomic DNA are known in the art.

The term "preferred off-nucleotides" or "off-nucleotide preferences" can be used interchangeably and refers to nucleotides that are located at the same position relative to the nucleotides of the target recognition site, but are more prevalent in the identified genomic off-target recognition sites. In some aspects, the preferred off-nucleotide when placed into the target recognition site is cleaved at a higher percentage than the target recognition site.

An "off-target recognition site locus" is the position on a chromosome comprising the off-target recognition site. Preferably, the off-target recognition site locus is within 0, 50, 100, 200, 300, 400, 500, 600, 700, 800, 900 or 1000 base pairs of the off-target recognition site.

Numbering of an amino acid or nucleotide polymer corresponds to numbering of a selected amino acid polymer or nucleic acid when the position of a given monomer component (amino acid residue, incorporated nucleotide, etc.) of the polymer corresponds to the same residue position in a selected reference polypeptide or polynucleotide.

As used herein, a "genomic region of interest" is a segment of a chromosome in the genome of a plant that is desirable for introducing a polynucleotide of interest or trait of interest. The genomic region of interest can include, for example, one or more polynucleotides of interest. Generally, a genomic region of interest of the present invention comprises a segment of chromosome that is 0-15 centimorgan (cM).

As used herein, a "polynucleotide of interest" within a genomic region of interest is any coding and/or non-coding portion of the genomic region of interest including, but not limited to, a transgene, a native gene, a mutated gene, and a genetic marker such as, for example, a single nucleotide polymorphism (SNP) marker and a simple sequence repeat (SSR) marker.

As used herein, "physically linked," "in physical linkage", and "genetically linked" are used to refer to any two or more genes, transgenes, native genes, mutated genes, alterations, target sites, markers, and the like that are part of the same DNA molecule or chromosome.

As used herein, an "isolated" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture media components when produced by recombinant techniques, or substantially free of chemical precursors or other molecules when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest molecules.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene, is recombinant.

The terms "recombinant polynucleotide", "recombinant nucleotide", "recombinant DNA" and "recombinant DNA construct" are used interchangeably herein. A recombinant construct comprises an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from Zea mays would be heterologous if inserted into the genome of an Oryza sativa plant, or of a different variety or cultivar of Zea mays; or a polynucleotide obtained from a bacterium was introduced into a cell of a plant), or sequence (e.g., a polynucleotide sequence obtained from Zea mays, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, one or more regulatory region (s) and/or a polynucleotide provided herein may be entirely synthetic.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

The term "adjacent", when used in reference to relative positions of a first nucleotide (or plurality of nucleotides) and a second nucleotide (or plurality of nucleotides), means that the number of nucleotides between the first and second nucleotides is 1, 2, 3, 4, 5, 6, 7, 8, 9, 10, between 10 and 20, 20, between 20 and 30, 30, between 30 and 40, 40 between 40 and 50, 50, between 50 and 75, 75, between 75 and 100, 100, between 100 and 150, 150, between 150 and 200, 200, between 200 and 250, 250, between 250 and 300, 300, between 300 and 350, 350, between 350 and 400, 400, between 400 and 450, 450, between 450 and 500, 500, between 500 and 750, 750, between 750 and 1000, 1000, between 1000 and 1500, 1500, or between 1500 and 2000 nucleotides.

Sequence Comparisons

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

As used herein, "comparison window" makes reference to a contiguous and specified segment of a polypeptide or polynucleotide sequence, wherein the polypeptide or polynucleotide sequence in the comparison window may comprise additions or deletions (i.e., gaps) compared to the reference sequence (which does not comprise additions or deletions) for optimal alignment of the two polypeptides or polynucleotides. Generally, the comparison window is at least 5, 10, 15, or 20 contiguous amino acids or nucleotides in length, or it can be 30, 40, 50, 100, or longer. Those of skill in the art understand that to avoid a high similarity to a reference sequence due to inclusion of gaps in the polypeptide or polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 872264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, California, USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTP protein searches can be performed using default parameters.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=S and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program. Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases. "BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence. It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percent sequence identity" means the value determined by comparing two aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment. Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides).

Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Double-Strand-Break-Inducing Agents

The term "double-strand-break-inducing agent" as used herein refers to any composition which produces a double-strand break in a target sequence in the genome of an organism. Double-strand-break-inducing agents may be proteins that include but are not limited to: endonucleases such as meganucleases, (US patent application 2332 and BB1990), zinc finger nucleases (Kim, Y. G., J. Cha, et al. (1996). "Hybrid restriction enzymes: zinc finger fusions to FokI cleavage;) Cas endonucleases (WO2007/025097 application published Mar. 1, 2007) and TALENs (Christian, M., T. Cermak, et al. 2010. Targeting DNA double-strand breaks with TAL effector nucleases. Genetics 186(2): 757-61).

In some aspects, one double-strand-break-inducing agent may be compared to another double-strand-break-inducing agent (a "reference double-strand-break-inducing agent" or "reference DSB agent"). In some aspects, the DSB agent itself is compared to a reference DSB agent. In some aspects, the activity or a characteristic of one DSB agent is compared to the activity or characteristic of a reference DSB agent. In some aspects, the DSB created by one DSB agent is compared to the DSB created by a reference DSB agent. The reference DSB agent may differ from the DSB agent that is compared to it in any of a number of ways, including but not limited to: derivation, origin, organism of identification, composition, nucleotide sequence, amino acid sequence, molecular structure, molecular activity, phylogenetic relationship, or class of molecule.

An "engineered double-strand-break-inducing agent" refers to any double-strand-break-inducing agent that is engineered (modified or derived) from its native form to specifically recognize and induce a double-strand break in the desired recognition site. Thus, an engineered double-strand-break-inducing agent can be derived from a native, naturally-occurring nuclease or it could be artificially created or synthesized. The modification of the nuclease can be as little as one nucleotide. In some embodiments, the engineered double-strand-break-inducing agent induces a double-strand break in a recognition site, wherein the recognition site was not a sequence that would have been recognized by a native (non-engineered or non-modified) double-strand-break-inducing agent. Producing a double-strand break in a recognition site or other DNA can be referred to herein as "cutting" or "cleaving" the recognition site or other DNA.

Restriction Endonucleases

Endonucleases include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, DC).

Meganucleases

A "meganuclease" refers to a homing endonuclease, which like restriction endonucleases, bind and cut at a specific recognition site, however the recognition sites for meganucleases are typically longer, about 18 bp or more. In some embodiments of the invention, the meganuclease has been engineered (or modified) to cut a specific endogenous recognition sequence, wherein the endogenous target sequence prior to being cut by the engineered double-strand-break-inducing agent was not a sequence that would have been recognized by a native (non-engineered or non-modified) endonuclease.

A "meganuclease polypeptide" refers to a polypeptide having meganuclease activity and thus capable of producing a double-strand break in the recognition sequence.

Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing open reading frames, introns, and inteins, respectively. For example, intron-, intein-, and free-standing gene encoded meganuclease from *Saccharomyces cerevisiae* are denoted I-SceI, PI-SceI, and F-SceII, respectively. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Examples of meganucleases include, but are not limited to: I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-Ppol, PI-Pspl, F-SceI, F-SceII, F-Suvl, F-Teel, F-TevII, I-Amal, I-Anil, I-ChuI, I-Cmoel, I-Cpal, I-CpaII, I-Csml, I-Cvul, I-CvuAIP, I-Ddil, I-DdiII, I-Dirl, I-Dmol, I-Hmul, I-HmuII, I—HsNIP, I-LlaI, I-Msol, I-Naal, I-NanI, I-NcIIP, I-NgrIP, I-NitI, I-Njal, I-Nsp236IP, I-PakI, I-PboIP, I-PcuIP, I-PcuAI, I-PcuVI, I-PgrIP, I-PobIP, I-Porl, I-PorIIP, I-PbpIP, I-SpBetaIP, I-ScaI, I-SexIP, I-Spoml, I-SpomCP, I-SpomIP, I-SpomIIP, I-SquIP, I-Ssp6803I, I-SthPhiJP, I-SthPhiST3P, I-SthPhiSTe3bP, I-TdeIP, I-Teel, I-TevII, I-TevIII, I-UarAP, I-UarHGPAIP, I-UarHGPA13P, I-VinIP, I-ZbiIP, PI-Mtul, PI-MtuHIP PI-MtuHIIP, PI-Pful, PI-PfuII, PI-Pkol, PI-PkoII, PI-Rma43812IP, PI-SpBetaIP, PI-SceI, PI-TfuI, PI-TfuII, PI-Thyl, PI-TliI, PI-TliII, or any functional variants or fragments thereof Argonautes Small non-coding RNAs are one type of contributor to gene regulation, and require a unique class of proteins called Argonautes. Argonaute proteins are highly specialized binding modules that can bind small non-coding RNAs and control protein synthesis, affect messenger RNA stability and even participate in the production of a new class of small RNAs, Piwi-interacting RNAs. Argonautes coordinate downstream gene-silencing events by interacting with other protein factors.

First identified in plants and subsequently discovered to be ubiquitous in many organisms, Argonaute proteins are defined by the presence of PAZ (Piwi-Argonaute-Zwille) and PIWI domains. They are evolutionarily conserved and can be phylogenetically subdivided into the Ago subfamily and the Piwi subfamily. Ago proteins are ubiquitously expressed and bind to siRNAs or miRNAs to guide post-transcriptional gene silencing either by destabilization of the mRNA or by translational repression. The expression of Piwi proteins is mostly restricted to the germ line and Piwi proteins associate with piRNAs to facilitate silencing of mobile genetic elements.

Many Argonaute proteins bind RNA guides to cleave foreign RNA, while others are capable of cleaving plasmid and genomic DNA. Natronobacterium gregoryi Argonaute uses 5' phosphorylated DNA guides (rather than the RNA guides employed by Cas9 or Cpf1), without requiring a PAM sequence, to randomly remove 1-20 nucleotides from the cleavage site specified by the gDNA. For a review of Argonaute proteins, see, for example Willkomm et al., "DNA silencing by prokaryotic Argonaute proteins adds a new layer of defense against invading nucleic acids", FEMS Microbiology Reviews doi: 10.1093/femsre/fuy010 20 Mar. 2018.

TAL Effector Nucleases (TALENs)

TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

Zinc-Finger Endonucleases

Zinc fingers are structural domains found in eukaryotic proteins which control gene transcription. The zinc finger domain of the $Cys_2His_2$ class of ZFPs is a polypeptide structural motif folded around a bound zinc ion, and has a sequence of the form —$X_3$-Cys-$X_{2-4}$-Cys-$X_{12}$-His-$X_{3-5}$-His-$X_4$- (wherein X is any amino acid). The zinc finger is an independent folding domain which uses a zinc ion to stabilize the packing of an antiparallel β-sheet against an α-helix. There is a great deal of sequence variation in the amino acids designated as X, however, the two consensus histidine and cysteine residues are invariant. Although most ZFPs have a similar three-dimensional structure, they bind polynucleotides having a wide range of nucleotide sequences. The binding of the zinc finger domain is dependent on the sequence of the polynucleotides other than those which directly contact amino acids within the zinc finger domain.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms.

Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides.

Cas Endonucleases

As used herein, the term "Cas gene" refers to a gene that is generally coupled, associated or close to or in the vicinity of flanking CRISPR loci.

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, Science 327:167-170; WO2007025097, published 1 Mar. 2007). A CRISPR locus can consist of a CRISPR array, comprising short direct repeats (CRISPR repeats) separated by short variable DNA sequences (called spacers), which can be flanked by diverse Cas (CRISPR-associated) genes.

Cas endonucleases, either as single effector proteins or in an effector complex with other components, unwind the DNA duplex at the target sequence and optionally cleave at least one DNA strand, as mediated by recognition of the target sequence by a polynucleotide (such as, but not limited to, a crRNA or guide RNA) that is in complex with the Cas effector protein. Such recognition and cutting of a target sequence by a Cas endonuclease typically occurs if the correct protospacer-adjacent motif (PAM) is located at or adjacent to the 3' end of the DNA target sequence.

Many Cas endonucleases have been described to date that can recognize specific PAM sequences (WO2016186953 published 24 Nov. 2016, WO2016186946 published 24 Nov. 2016, and Zetsche B et al. 2015. Cell 163, 1013) and cleave the target DNA at a specific position.

Cas endonucleases may be capable of forming a complex with a guide polynucleotide (e.g., guide RNA or gRNA) that is capable of recognizing, binding to, and optionally nicking, unwinding, or cleaving all or part of a target sequence. In some aspects, the guide polynucleotide/Cas endonuclease complex is capable of introducing a double-strand-break into a target polynucleotide. In some aspects, the guide polynucleotide comprises solely RNA, solely DNA, a chimeric molecule comprising both DNA and RNA, and/or comprises a chemically modified nucleotide. The guide polynucleotide (e.g., guide RNA) may be a single guide RNA (sgRNA) that is capable of binding to a sequence on the target polynucleotide.

Alternatively, a Cas endonuclease herein may lack DNA cleavage or nicking activity, but can still specifically bind to a DNA target sequence when complexed with a suitable RNA component. (See also U.S. Patent Application US20150082478 published 19 Mar. 2015 and US20150059010 published 26 Feb. 2015).

Cas endonucleases may occur as individual effectors (Class 2 CRISPR systems) or as part of larger effector complexes (Class I CRISPR systems).

Cas endonucleases include, but are not limited to, Cas endonucleases identified from the following systems: Class 1, Class 2, Type I, Type II, Type III, Type IV, Type V, and Type VI. In some aspects, the Cas endonuclease is Cas3 (a feature of Class 1 type I systems), Cas9 (a feature of Class 2 type II systems) or Cas12 (Cpf1) (a feature of Class 2 type V systems).

Cas endonucleases and effector proteins can be used for targeted genome editing (via simplex and multiplex double-strand breaks and nicks) and targeted genome regulation (via tethering of epigenetic effector domains to either the Cas protein or sgRNA. A Cas endonuclease can also be engineered to function as an RNA-guided recombinase, and via RNA tethers could serve as a scaffold for the assembly of multiprotein and nucleic acid complexes (Mali et al., 2013, *Nature Methods Vol.* 10: 957-963).

A Cas endonuclease, effector protein, functional variant, or a functional fragment thereof, for use in the disclosed methods, can be isolated from a native source, or from a recombinant source where the genetically modified host cell is modified to express the nucleic acid sequence encoding the protein. Alternatively, the Cas protein can be produced using cell free protein expression systems, or be synthetically produced. Effector Cas nucleases may be isolated and introduced into a heterologous cell, or may be modified from its native form to exhibit a different type or magnitude of activity than what it would exhibit in its native source. Such modifications include but are not limited to: fragments, variants, substitutions, deletions, and insertions.

Fragments and variants of Cas endonucleases and Cas effector proteins can be obtained via methods such as site-directed mutagenesis and synthetic construction. Methods for measuring endonuclease activity are well known in the art such as, but not limiting to, WO2013166113 published 7 Nov. 2013, WO2016186953 published 24 Nov. 2016, and WO2016186946 published 24 Nov. 2016.

Functional Association of a Double-Strand-Break-Inducing Agent with a Target Polynucleotide A double-strand-break-inducing agent described herein may be introduced to a target polynucleotide to create a "functional association". A "functional association" means that the DSB agent is introduced to a target polynucleotide molecule, may optionally bind to it, and is capable of producing a double-strand-break on the backbone of the target polynucleotide to which it is introduced. The position (location with respect to the polynucleotide sequence) and nature (blunt-end, sticky-end, or mixed) of the double-strand break is dependent upon the exact DSB agent used. Said functional association may be accomplished in an in vitro, ex vivo, or in vivo environment.

Compositions Comprising a DSB Agent

In some aspects, the DSB agent can be provided as a polypeptide, that can be purified and substantially free of other molecules, or can be in association with one or more heterologous components. In one embodiment, the DSB agent is a polypeptide and a polynucleotide. In one embodiment, the DSB agent is a fusion protein, comprising two or more domains, wherein one domain can effect the cleavage of a target polynucleotide. In one embodiment, the DSB agent is a plurality of polypeptides.

In some aspects, the DSB agent can be provided via a polynucleotide encoding the DSB agent polypeptide. Such a polynucleotide encoding may optionally be modified to substitute codons having a higher frequency of usage in a particular host cell or organism, as compared to the naturally-occurring polynucleotide sequence. For example, the polynucleotide encoding the DSB agent can be modified to substitute codons having a higher frequency of usage in a maize or soybean plant, as compared to the naturally occurring polynucleotide sequence.

A double-strand-break-inducing agent polynucleotide may be provided in expression cassettes for expression in a cell of interest. The cassette can include 5' and 3' regulatory sequences operably linked to an endonuclease polynucleotide or functional variant or functional fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally comprise at least one additional gene to be co-transformed into the organism. Alternatively, the additional gene(s) can be provided on multiple expression cassettes. Such an expression cassette is provided with a plurality of restriction sites and/or recombination sites for insertion of the endonuclease polynucleotide or functional variant or functional fragment thereof to be under the transcriptional regulation of the regulatory regions. The expression cassette may additionally comprise one or more selectable marker gene(s).

The expression cassette can include in the 5'-3' direction of transcription, a transcriptional and translational initiation region (i.e., a promoter), an endonuclease polynucleotide or functional variant or functional fragment thereof, and a transcriptional and translational termination region (i.e., termination region) functional in the recipient organism. The regulatory regions (i.e., promoters, transcriptional regulatory regions, and translational termination regions) and/or the endonuclease polynucleotide or functional variant or functional fragment thereof may be native/analogous to the host cell or to each other. Alternatively, the regulatory regions and/or the endonuclease polynucleotide of or functional variant or functional fragment thereof may be heterologous to the host cell or to each other.

While it may be desired in some embodiments to express the sequences using heterologous promoters, the native promoter sequences to the polynucleotide encoding the double-strand-break-inducing agent may alternatively be used. Such constructs can change expression levels of the polynucleotide in the cell. Thus, the phenotype of recipient cell can be altered.

Where appropriate, the polynucleotides may be optimized for increased expression in the recipient cell or organism. That is, the polynucleotides can be synthesized using organism-preferred codons for improved expression. See, for example, Campbell and Gown (1990) *Plant Physiol.* 92:1-11 for a discussion of host-preferred codon usage in plants.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand- Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. The above list of selectable marker genes is not meant to be limiting. Any selectable marker gene may be used with any of the methods or compositions disclosed herein.

In some aspects, the cell or organism is derived from a prokaryote, for example but not limited to *E. coli*.

In some aspects, the cell or organism is derived from an animal, for example a mammalian cell, for example a human cell. In some aspects, the cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV 40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cells RHP, and human nasopharyngeal tumor KB cell.

In some aspects, the cell or organism is derived from a plant. In some aspects, the plant is a monocot. In some aspects, the plant is a dicot. Examples of plant species of interest include, but are not limited to, *Arabidposis*, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifoha*), almond (*Prunus amygdalus*), sugar beets (*Beta vulgaris*), sugarcane (*Saccharum* spp.), oats, barley, vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*).

Methods of Introduction

The double-strand-break-inducing agent ("DSB agent") may be introduced to, or provided to, the target polynucleotide by any means known in the art.

In one example, the DSB agent is provided to an isolated polynucleotide in vitro. The isolated polynucleotide may be obtained or derived from a source organism, tissue, or individual cell, and may additionally comprise a heterologous component.

In one example, a cell, yeast, animal, or plant having the target or off-target recognition site in its genome is provided. The DSB agent may be transiently expressed or the polypeptide itself can be directly provided to the cell. Alternatively, a nucleotide sequence capable of expressing the DSB agent may be stably integrated into the genome of the plant. In the presence of the corresponding target or off-target recognition site and the DSB agent, a donor DNA can be inserted into the transformed plant's genome. Alternatively, the different components may be brought together by sexually crossing transformed plants. Thus, a sequence encoding a DSB agent and/or target or off-target recognition site can be sexually crossed to one another to allow each component of the system to be present in a single plant. The DSB agent may be under the control of a constitutive or inducible promoter. Examples of such are well known in the art.

Various methods can be used to introduce a sequence of interest such as, any of the double-strand-break-inducing agents into a cell. "Introducing" is intended to mean presenting to the cell, organism, or part the polynucleotide or polypeptide in such a manner that the sequence gains access to the interior of a cell of the organism or part. The methods of the invention do not depend on a particular method for introducing a sequence, only that the polynucleotide or polypeptides gains access to the interior of at least one cell. Methods for introducing polynucleotide or polypeptides into cells are known in the art including, but not limited to, stable transformation methods, transient transformation methods, and virus-mediated methods.

Generally, such methods involve incorporating a nucleotide construct of the invention within a DNA or RNA molecule. It is recognized that the a DSB agent sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases.

"Stable transformation" is intended to mean that the nucleotide construct introduced into a cell integrates into the genome of the cell and is capable of being inherited by the progeny of the organism comprising said cell. "Transient transformation" is intended to mean that a polynucleotide is introduced into the cell and does not integrate into the genome of the cell, or that a polypeptide is introduced into a cell instead of a polynucleotide encoding the polypeptide.

In some embodiments, the DSB agent sequence, or functional variant or fragments thereof, may be provided to a cell or part of an organism using a variety of transient transformation methods. Such transient transformation methods include, but are not limited to, the introduction of the DSB agent protein or functional variants and fragments thereof directly into a yeast cell or plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784.

In some embodiments, the DSB agent nucleotide sequence, or a functional variant or functional fragment thereof, may be provided to a cell or part of an organism using a variety of stable transformation methods. Suitable methods of introducing polypeptides and polynucleotides into cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879, 918; 5,886,244; and, 5,932,782). Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference. Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853. Other methods to target polynucleotides are set forth in WO 2009/114321, which describes "custom" DSB agents produced to modify plant genomes, in particular the genome of maize. See, also, Gao et al. (2010) *Plant Journal* 1:176-187.

The cells that have been transformed with the DSB agent may be further analyzed, or may be grown into whole organisms in accordance with conventional ways. See, for example, McCormick et al. (1986) *Plant Cell Reports* 5:81-84.

Qualitative and Quantitative Assessment of Functional Associations

The term "activity" as used herein refers to the ability of a DSB agent to produce a double-strand break at a desired recognition sequence. Producing the double-strand break in a recognition sequence or other polynucleotide can be referred to herein as "cutting" or "cleaving" the recognition sequence or other DNA.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800, 159; herein incorporated by reference).

Probes and primers are of sufficient nucleotide length to bind to the target DNA sequence and specifically detect and/or identify a polynucleotide encoding a DSB agent polypeptide or functional variant or functional fragment thereof as describe elsewhere herein. It is recognized that the hybridization conditions or reaction conditions can be determined by the operator to achieve this result. This length may be of any length that is of sufficient length to be useful in a detection method of choice. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide.

Methods for preparing and using probes and primers are described, for example, in *Molecular Cloning: A Laboratory Manual*, 2nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 10 (Invitrogen); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

Cleavage by endonucleases usually generates cohesive ends, with 3' overhangs for LAGLIDADG meganucleases (Chevalier, B. S. and B. L. Stoddard. 2001. Homing endonucleases: structural and functional insight into the catalysts of intron/intein mobility. Nucleic Acids Res 29(18): 3757-74) and 5' overhangs for Zinc Finger nucleases (Smith, J., M. Bibikova, et al. 2000, Requirements for double-strand cleavage by chimeric restriction enzymes with zinc finger DNA-recognition domains. Nucleic Acids Res 28(17): 3361-9). FokI-based TALE-nucleases (TALENs) have a similar functional layout than Zinc-Finger Nucleases, with the Zinc-finger DNA binding domain being replaced by the TALE domain (Li, T., S. Huang, et al. 2011. TAL nucleases (TALNs): hybrid proteins composed of TAL effectors and FokI DNA-cleavage domain. Nucleic Acids Res 39(1): 359-72; Christian, M., T. Cermak, et al. 2010). Cleavage with Cas endonucleases such as Cas9 endonucleases can result in blunt ends.

Assays for DSB agent activity generally measure the overall activity and specificity of the DSB agent on polynucleotide substrates comprising the appropriate recognition site (length and composition) for that particular DSB agent. These polynucleotide substrates include but are not limited to genomic DNA and plasmid DNA.

In one embodiment, DSB agent activity can be measured, for example as described in Example 3 of U.S. Patent Application Publication No. US20160032297A1 published 4 Feb. 2016. Briefly, time-course digestions can be carried out at a temperature between or including 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., or 15° C., or even less than 15° C., or even greater than 37° C., on plasmid or genomic DNA comprising a DSB recognition site. The percent digestion of each sample (also referred to as % cleavage or to as % loss of DSB recognition sites) (indicative of DSB agent activity) can be determined by real-time PCR.

In one embodiment, DSB agent activity can also be measured using a yeast screening assay, for example as described in FIGS. 8 and 9 and Example 16 of U.S. Patent Application Publication No. US20160032297A1 published 4 Feb. 2016. Briefly, yeast cells with a functional Ade2 gene are white, whereas those lacking Ade2 function exhibit red pigmentation due to accumulation of a metabolite earlier in the adenine biosynthetic pathway resulting in red colonies with white sectors. The degree of white sectoring, sometimes extending to entire colonies, indicates the amount of DSB agent cutting activity. Since the sectoring phenotype is a qualitative measure of meganuclease activity, a 0-4 numerical scoring system was implemented. A score of 0 indicates that no white sectors (no DSB agent cutting) were observed; a score of 4 indicates completely white colonies (complete cutting of the recognition site); scores of 1-3 indicate intermediate white sectoring phenotypes (and intermediate degrees of recognition site cutting).

In one embodiment, DSB agent activity can also be measured in-planta by determining the Target Site (TS) mutation rate. Target site mutation rate is defined as: (number of events with target site modification/total number events)*100%.

A "control DSB agent" or "reference DSB agent" can be used interchangeably and refers to any DSB agent to which another is compared. Control DSB agents can include, but are not limited to, parental or wild-type DSB agents of the same type, or a DSB agent of a different type, that is benchmarked, or compared to, the control.

The characterization of a double-strand-break site of a polynucleotide is useful for a number of applications, including but not limited to: identification of a cleavage site for a DSB agent, identification of a recognition site for a DSB agent, sequencing of polynucleotides adjacent to said cleavage site for the identification of motifs such as PAM sequences, assessment of target recognition site and off-target recognition site cleavage by a particular DSB agent, creation of single nucleotide polymorphism (SNP) maps, comparison of fragments generated by different DSB agents to inform breeding applications, identification of genomic sites for transgene insertion, and identification of genomic sites for endogenous polynucleotide modification (insertion, deletion, substitution, or nucleotide alteration such as methylation, chemical modification, or covalent or ionic interaction with another atom or molecule).

The qualitative and quantitative characteristics of the DSB agent cleavage activity and target polynucleotide may be assessed.

Qualitative characteristics may include: position of the double-strand-break site, identification of target recognition site, identification of an off-target recognition site, number of times a double-strand-break cleavage event occurs within a given polynucleotide molecule, nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site. Polynucleotide compositions may include a polynucleotide of interest, which may be selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a non-coding regulatory element, a marker, a complex trait locus, a QTL, and a heterologous polynucleotide.

Quantitative characteristics may include: percent cleavage activity of the double-strand-break inducing agent, and the number of nucleotides comprising the polynucleotide of interest.

In some embodiments, the value of a qualitative or quantitative characteristic is compared to the value of the same characteristic of a reference double-strand-break-inducing agent. In some embodiments, said quantitative value is increased as compared to the reference double-strand-break-inducing agent. In some embodiments, said quantitative value is decreased as compared to the reference double-strand-break-inducing agent. In some embodiments, said qualitative value is the same as that of the reference double-strand-break-inducing agent. In some embodiments, said qualitative value is different than that of the reference double-strand-break-inducing agent.

The methods and compositions provided herein improve the ability of sequencing applications to sensitively detect double strand breaks in a polynucleotide generated by a double-strand-break-inducing agent, while reducing the detection of random ends generated by nonspecific cleavage of the polynucleotide. In some aspects, the information obtained from the methods herein may be used to improve the number of double-strand breaks created by a double-strand-break-inducing agent compared to the number of randomly-generated cuts/ends.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific embodiments of some aspects of the invention. The examples are offered for illustrative purposes only, and are not intended to limit the scope of the invention in any way. Efforts have been made to ensure accuracy with respect to numbers used (e.g., amounts, temperatures, etc.), but some experimental error and deviation should, of course, be allowed for. Unit abbreviations include kb for kilobases, ul for microliters, nM for nanomolar, g for relative centrifugal force (gravitational force unit).

In one aspect, a method is provided to identify the qualitative and/or quantitative characteristics of the cleavage sites within genomic DNA, as well as to characterize nuclease activity and specificity. Cells edited with a double-strand-break-inducing agent, such as a Cas endonuclease as part of a Cas-gRNA complex, are assayed for mutations at each cut site using amplicon sequencing. The number of sites identified may depend on many factors, such as sgRNA sequence and nuclease concentration.

In the following examples, *S. pyogenes* Cas9 (SEQ ID NO: 1) was utilized as the DSB agent. Any DSB agent may be used to generate double-strand breaks in a polynucleotide, for analysis according to the methods described herein. The following examples describe one embodiment of the invention. It is understood that in vitro reactions may be carried-out in a different buffer, at different temperatures, and/or length(s) of incubation to foster ideal cleavage conditions for different DSB agents.

Prior to cleavage with a DSB agent, it may be desirable to ascertain the nature of cleavage (i.e., creation of sticky-ends or blunt-ends) created by the DSB agent on the target polynucleotide. Any method known in the art can be used, for example, see the method for run-off sequencing in Karvelis et al., "Rapid Characterization of CRISPR-Cas9 Protospacer Adjacent Motif Sequence Elements", *Genome Biology* 16:253, 2015.

Figure 1:
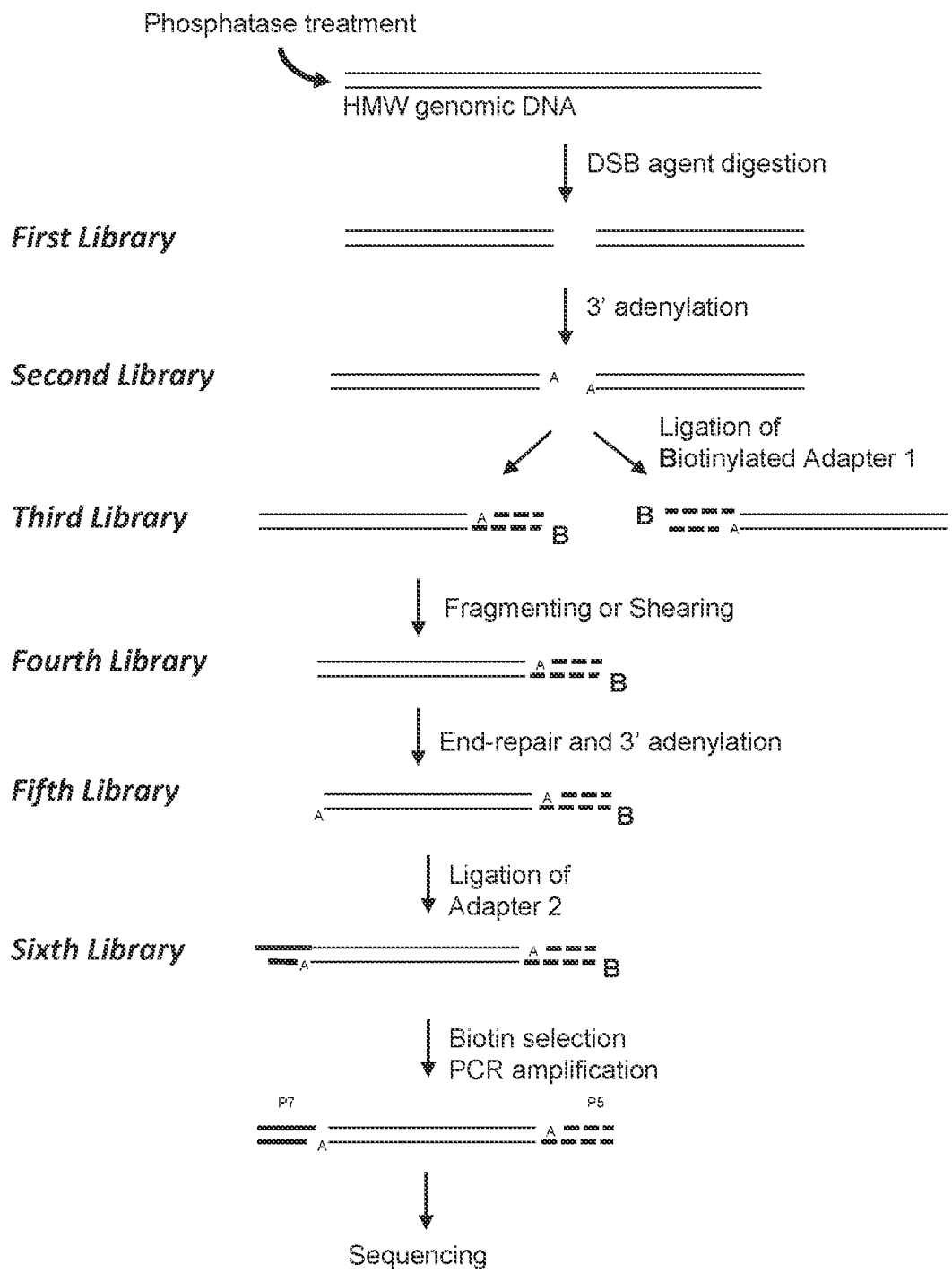
FIG. 1 depicts one embodiment of the disclosed method, for the identification and characterization of a double-strand break produced by a double-strand-break-inducing agent capable of effecting a "blunt-end" cut in a double-stranded polynucleotide.

One embodiment of the disclosed method is depicted in FIG. 1, for the identification and characterization of a double-strand break produced by a double-strand-break-inducing agent capable of effecting a "blunt-end" cut in a double-stranded polynucleotide.

Figure 2:
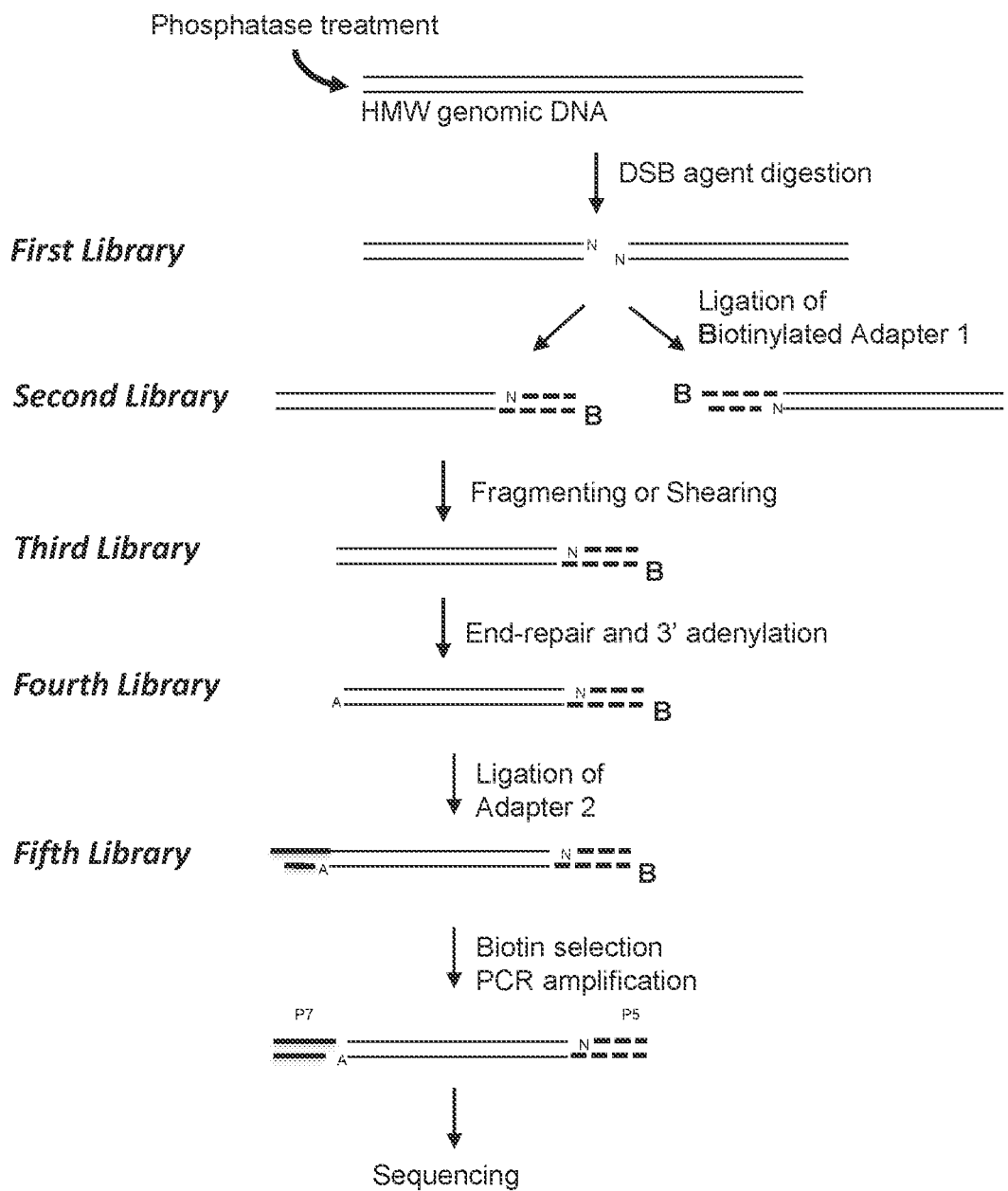
FIG. 2 depicts one embodiment of the disclosed method, for the identification and characterization of a double-strand break produced by a double-strand-break-inducing agent capable of effecting a "sticky-end" cut in a double-stranded polynucleotide.

One embodiment of the disclosed method is depicted in FIG. 2, for the identification and characterization of a double-strand break produced by a double-strand-break-inducing agent capable of effecting a "sticky-end" cut in a double-stranded polynucleotide.

One embodiment of the disclosed method is depicted in FIG. 3 for the identification and characterization of a double-strand break produced by a double-strand-break-inducing agent, wherein the nature of the cleavage (e.g., blunt-end or sticky-end) is either not known, or the activity of the DSB agent is mixed or incomplete.

One embodiment of the disclosed method is depicted in FIG. 4, for the identification and characterization of a double-strand break produced by a double-strand-break-inducing agent capable of effecting a "blunt-end" cut in a double-stranded polynucleotide.

Example 1: Isolation and Purification of a Target Polynucleotide

In this example, isolation and purification of a target polynucleotide sequence is described. In some aspects, the target polynucleotide is isolated and purified from genomic DNA of an organism, tissue, or cell.

The QIAGEN Blood & Cell Culture DNA Maxi Kit (QIAGEN #13362) was used to obtain high molecular weight (HMW) genomic DNA (gDNA) from B73 maize leaf tissue cells per standard protocols well known in the art. Although plant cells were used to demonstrate the method, any cell could be used, including any eukaryotic cell, any mammalian cell, any human cell. Alternatively, double-strand polynucleotide(s) may be synthetically created, derived from a virus, be present as a plasmid, or be isolated and purified from a non-nuclear source such as cellular cytoplasm or another organelle (i.e. chloroplast or mitochondrion). A suspension of approximately $10^7$ cells/mL was prepared in a test tube. For each 10 mL suspension, 10 mL ice cold Cl buffer was added. The tube was mixed by inverting several times and incubated on ice for 10 minutes.

The lysed cells were centrifuged at 4 degrees Celsius for 15 minutes at 1300×g. The supernatant was discarded. The pellet was washed with 2 mL of ice cold Cl buffer, with 6 mL of ice cold water. The suspension was resuspended by vortexing, and centrifuged again for 15 minutes at 4 degrees Celsius at 1300×g. The supernatant was discarded. The pellet was resuspended in 10 mL G2 buffer by vortexing for 10-30 seconds at maximum speed, to create a digested suspension sample.

200 microliters of QIAGEN Protease was added, and the solution incubated at 50 degrees Celsius for 30-60 minutes.

A QIAGEN genomic-tip 500/G column was equilibrated with 10 mL of QBT, and allowed to empty by gravity flow.

The digested suspension sample was vortexed for 10 seconds at maximum speed and applied to the equilibrated Genomic-tip column, and allowed to empty by gravity flow. The column was washed twice with 15 mL QC each. Genomic DNA was eluted with 15 mL Buffer QF. In some embodiments, the QF buffer was preheated to 50 degrees Celsius to increase yields. The eluted DNA was precipitated by adding 10.5 mL room temperature isopropanol (Fisher Scientific, BP26181) to the elution, mixed by inverting the tube for 10-20 times, and centrifuged for 15 minutes at 4 degrees Celsius at >5000×g.

After centrifugation, the supernatant was removed, and the pellet washed with 4 mL cold 70% ethanol. The solution was centrifuged for 10 minutes at >5000×g, and the supernatant removed.

The pellet was allowed to air dry for 5-10 minutes, then resuspended in 0.5-1.0 mL suitable buffer (TE or 10 mM Tris-HCl), and incubated on a shaker overnight, or alternatively at 55 degrees Celsius for 1-2 hours.

Example 2: Quantification and Qualification of HMW gDNA

In this example, the isolated and purified genomic DNA was verified to be intact and of high molecular weight (greater than 50 kb).

The DNA sample obtained from Example 1 was allowed to come to room temperature and mixed well by inverting. In some aspects, mixing was accomplished by pipetting up and down.

A 1% agarose gel was prepared by adding 0.5 g agarose (BioExpress, 07-10-500G) to 50 mL 1×TAE buffer (50× Tris/Acetic Acid/EDTA, BioRad, 161-0743) per gel. The mixture was heated and swirled until the agarose dissolved into solution, and 10,000×SYBR® Safe DNA Gel Stain (Thermo Scientific, S33102) was added. The gel was poured and allowed to cool for 30 minutes. To load the gel, 10 microliters of DNA ladder (100 bp DNA Ladder (NEB, N3231L), Quick-Load® 1 kb Extend DNA Ladder (NEB, N3239S)) and 0.5-1.5 micrograms of HMW gDNA samples were mixed with Gel Loading Dye (NEB, B7021S). The gel was run at 85-100V for 1-2 hours. The primary band of the gDNA lanes demonstrated that the isolated and purified gDNA was high molecular weight (over 50 kb).

Example 3: Digestion of HMW gDNA with a DSB Agent

In this example, a DNA sample such as the HMW gDNA isolated and purified in Example 1, formed a functional association with a Cas9 Endonuclease and sgRNA RNP complex. In other embodiments, a different Cas endonuclease, or a meganuclease, or a zinc finger nuclease, or a TAL effector nuclease, or other DSB agent may be used to cleave a polynucleotide.

A Cas9 Cleavage Buffer (CCB) was prepared according to the following: 100 mM HEPES (Sigma Aldrich, H3375) pH 7.4, 750 mM KCl (Sigma Aldrich, 746436), 50 mM $MgCl_2$ (Sigma Aldrich, M1028), and 25% glycerol (Sigma Aldrich, G5516).

Frozen reagents, such as purified HMW gDNA and single guide RNA (sgRNA), were allowed to thaw on ice.

Approximately 3 micrograms of HMW gDNA was treated with 5 units Antarctic phosphatase (New England Biolabs M0289S) at 37 degrees Celsius for 30 minutes, followed by enzymatic inactivation at 80 degrees Celsius for 2 minutes. The addition of phosphatase reduces the presence of randomly broken DNA ends detected in the assay, which provides greater sensitivity for the detection of both target- and off-target recognition-sites created by the DSB agent, and allows a reduction in sequencing depth compared to methods not employing a phosphatase treatment of the DNA. Enrichment of the target site was demonstrated to be approximately 8-fold over the control protocol lacking the phosphatase step (FIG. 6).

Cas9 (SEQ ID NO: 1) was diluted in the CCB and water such that each reaction was 15 microliters of 3.3×CCB and 3.3× final Cas9 concentration.

The single guide RNA (sgRNA) sequence 5'-GGCGGCGGCGAGGTAGTGCG-3' (SEQ ID NO: 2) was designed to target a region of Chromosome 2 of the *Zea mays* genome. The sgRNA was diluted to a target concentration of 10× final RNP concentration in 15 microliters molecular biology grade water (Sigma-Aldrich, W4502). 480 nM sgRNA was denatured by heating to 95 degrees Celsius for 2 minutes, then allowed to cool to room temperature for approximately 5 minutes.

The diluted Cas9 was mixed with the sgRNAs and incubated at 37 degrees Celsius for 10 minutes. The RNP concentration varied from 0.25-1.024 nM, with a targeted sgRNA:Cas9 ratio of at least 3:1. In one aspect, the relative concentrations of gRNA and Cas9 was 64 nM Cas9 and 192 nM gRNA.

The dephosphorylated BMW gDNA was added to each RNP reaction. Each reaction was incubated for 37 degrees Celsius for 4 hours prior to the next step. Optionally, each reaction was then held at 4 degrees Celsius overnight.

Each reaction was terminated by adding 6.8 microliter of a Proteinase K/RNAse A mixture that was prepared according to the following: 0.5 microliters of 20 mg/mL Proteinase K (Denville Scientific, CB3210-5), 2.2 microliters of 20 mg/mL RNAse A (Sigma-Aldrich, R4642-10MG), 1.4 microliters 5×CCE buffer, 2.7 microliters molecular biology grade water. The termination reaction was mixed well by pipetting, and incubated at 37 degrees Celsius for 20 minutes followed by incubation at 55 degrees Celsius for 20 minutes.

Example 4: DNA Cleanup #1

The terminated reaction of Example 3 was cleaned up according to the following procedure. One volume (56.8 microliters) of SPRISelect reagent (SPRISelect Reagent Kit (Beckman Coulter, B23318)) or AMPure XP beads was added to the terminated reaction sample obtained from Example 3.

The reaction mixture was mixed well to ensure that the beads and the gDNA were well-mixed. The reaction mixture was incubated for 5 minutes at room temperature. The sample was placed on a compatible magnetic stand, and the beads were allowed to pellet for 5 minutes. The supernatant was removed, and the remaining components washed twice with 175 microliters freshly prepared 85% ethanol (prepared from ethanol, 200 proof, Molecular Biology Grade (Fisher Scientific, 3916EA)), with supernatant removed after 30 seconds for each wash. The ethanol was allowed to evaporate for approximately 10 minutes, until the beads were dry. The beads were removed from the magnetic stand, and 50 microliters of water was added to the vessel, and mixed until the beads were resuspended. The reaction mixture was incubated at room temperature for 5 to 10 minutes. The reaction mixture was placed back on the magnetic stand, and the beads allowed to fully pellet. 45 microliters of the elution were transferred to a fresh tube for subsequent processing (see Example 5). Optionally, the sample was frozen at −20 degrees Celsius.

Example 5: 3' Adenylation and Adapter #1 Ligation

To capture genomic DNA off-target recognition sites for DSB agents where most of the cleaved products result in blunt-ended termini, such as for Cas9 endonuclease (Gasiunas et al. (2012) Proc. Natl. Acad. Sci. USA 109:E2579-86, Jinek et al. (2012) Science 337:816-21), the addition of an adenine to the 3' termini of cleaved genomic DNA off-target recognition site(s) was performed. In this example, a single adenine is appended to the 3' end of each DNA molecule, enabling subsequent adapter ligation. Non-phosphorylated adapters comprising a complementary 3' thymine overhang were then used to selectively ligate to, and enrich for, the blunt-ended termini resulting from cleavage by the DSB agent.

If the nature (i.e., blunt-end or sticky-end) of the double-strand break created by the DSB agent is not known, then prior to adenylating, proceed with an end-repair step as follows. The NEBNext Ultra End Repair/dA-tailing module reagents (NEB, E7442L) were placed on ice (and allowed to thaw, if previously frozen). The 33 microliter end-repair reaction was assembled as follows: 27.7 microliters fragmented DNA, 3.3 microliters 10× end-repair reaction buffer, 1.5 microliters end-repair enzyme mix, and 0.5 microliters molecular biology grade water. The reaction was incubated for 30 minutes at 20 degrees Celsius, then incubated for 30 minutes at 65 degrees Celsius.

If the DSB agent creates sticky-end cuts, then adenylation is not performed, and ligation of the adapter is instead conducted by utilizing an appropriate nucleotide overhang complementary to the overhang on the sticky end of the polynucleotide, or by incubation with different molecules comprising all possible nucleotides complementary to any overhang of the sticky end of the polynucleotide. In some aspects, a library of adapters with a plurality of possible nucleotide overhangs is created. In some aspects, a library of adapters with different lengths of overhangs is created. If the composition of the nucleotide overhang of the stick ends is known, end repair prior to adapter #1 ligation is not necessary.

NEBNext® dA-tailing reagents (NEBNext® dA-tailing Kit (NEB, E6053L)) were removed from −20 degree Celsius storage and allowed to thaw on ice. Each 50 microliter adapter reaction was assembled according to the following: 42 microliters Cas9-treated gDNA (prepared as previously described), 5 microliters 10×dA-tailing reaction buffer (NEBNext® dA-tailing Kit (NEB, E6053L)), and 3 microliters Klenow fragment enzyme (New England Biolabs). The reaction mixture was incubated at 37 degrees Celsius for 30 minutes.

A 2× annealing buffer was prepared according to the following: 20 mM Tris pH 7.5 (prepared from Tris-HCl, pH 8.0 (Sigma Aldrich, T3038)), 100 mM NaCl (Sigma Aldrich, S5150), and 2 mM EDTA (Sigma-Aldrich, 03690-100ML).

Adapter #1 was assembled according to the following: 1 microliter 100 micromolar HPLC-purified biotinylated Adapter 1 Forward (SEQ ID NO: 3 for blunt-end adenylated polynucleotides or polynucleotides with a terminal A overhang, or SEQ ID NOs: 4, 5, or 6 for sticky-end non-adenylated polynucleotides with a terminal T, G, or C overhang), 1 microliter 100 micromolar Adapter 1 Reverse (SEQ ID NO:7), 8 microliters molecular biology grade water, and 10 microliters 2× annealing buffer. The 20 microliter Adapter #1 mixture was incubated for 5 minutes at 95 degrees Celsius, and allowed to cool to room temperature for approximately 45 minutes. The Adapter #1 oligos annealed to form a functional adapter.

A 50 microliter ligation reaction was assembled according to the following: 38 microliters dA-tailed DNA as prepared above, 2 microliters Adapter #1 prepared as above, 5 microliters 10×T4 DNA ligase buffer (NEB, B0202S), and 5 microliters NEB Quick Ligase (NEB Quick Ligation Kit (NEB, M2200L)). The ligation reaction was incubated for 30 minutes at 20 degrees Celsius, then incubated overnight at 16 degrees Celsius.

The resulting biotinylated-adapter-ligated DSB sites were then enriched for, sequenced, and identified as described below.

Example 6: DNA Cleanup #2

This example describes removing the residual, non-bound Adapter #1 from the ligation reaction of Example 5.

25 microliters (0.5× volume) SPRISelect reagent (SPRISelect Reagent Kit (Beckman Coulter, B23318)) or AMPure beads was added to the sample resulting from Example 5, and mixed well. The reaction mixture was incubated for 5 minutes at room temperature, and placed on a compatible magnetic stand. Beads were allowed to pellet for 5 minutes, and the supernatant was removed. The pellet was washed twice with 175 microliters freshly prepared 85% ethanol prepared from ethanol, 200 proof, Molecular Biology Grade (Fisher Scientific, 3916EA)), with supernatant removed after 30 seconds for each wash. The ethanol was allowed to evaporate for approximately 10 minutes, until the beads were dry. The beads were removed from the magnetic stand, and 50 microliters of water was added to the vessel, and mixed until the beads were resuspended. The reaction mixture was incubated at room temperature for 5 to 10 minutes. The reaction mixture was placed back on the magnetic stand, and the beads allowed to fully pellet. 45 microliters of the elution were transferred to a fresh tube for subsequent processing (see Example 7). Optionally, the sample was frozen at −20 degrees Celsius.

Example 7: gDNA Fragmentation

In this example, the cleaned-up Adapter #1 ligated gDNA library generated in Example 6 was fragmented to an appropriate size for sequencing (approximately 200-800 bp).

In one embodiment, NEBNext® dsDNA Fragmentase® reagent (NEB, M0348L) was removed from −20 degree Celsius storage and allowed to thaw on ice. A 50 microliter fragmentation reaction was assembled according to the following: 40 microliters Adapter #1-ligated DNA (as described in Examples 5 and 6), 5 microliters 10× dsFragmentase Buffer v2, 1.5 microliters dsFragmentase Enzyme, and 3.5 microliters molecular biology grade water. The reaction was incubated for one hour at 37 degrees Celsius, and immediately quenched with 12.5 microliters 0.5M EDTA, mixed by pipetting up and down. Improved results were obtained by diluting the reaction prior to cleanup (as described in Example 8), so 37.5 microliters of molecular biology grade water was added.

In another embodiment, the cleaned-up Adapter #1 ligated gDNA library generated in Example 6 was sheared to fragments of approximately 500 nucleotides in length with a Covaris 5220 ultrasonicator.

The mixture is then processed according to Example 8.

Example 8: DNA Cleanup #3

This example describes removing residual components from the fragmentation reaction of Example 7, when fragmentation was achieved via use of fragmentase. This example for DNA Cleanup step was not performed when fragmentation was achieved via sonication.

90 microliters (0.9× volume) of SPRISelect reagent (SPRISelect Reagent Kit (Beckman Coulter, B23318)) was added to the sample produced from Example 8. The reaction mixture was incubated for 5 minutes at room temperature, and placed on a compatible magnetic stand. Beads were allowed to pellet for 5 minutes, and the supernatant was removed. The pellet was washed twice with 175 microliters freshly prepared 85% ethanol prepared from ethanol, 200 proof, Molecular Biology Grade (Fisher Scientific, 3916EA)), with supernatant removed after 30 seconds for each wash. The ethanol was allowed to evaporate for approximately 10 minutes, until the beads were dry. The beads were removed from the magnetic stand, and 50 microliters of water was added to the vessel, and mixed until the beads were resuspended. The reaction mixture was incubated at room temperature for 5 to 10 minutes. The reaction mixture was placed back on the magnetic stand, and the beads allowed to fully pellet. 45 microliters of the elution were transferred to a fresh tube for subsequent processing (see Example 9). Optionally, the sample was frozen at −20 degrees Celsius.

The fragmented DNA was optionally visualized by gel electrophoresis (as per the protocol in Example 2).

Example 9: End-Repair and Adapter #2 Ligation

In this example, an adenine is appended to the 5' end of each DNA molecule produced in Example 8, enabling subsequent adapter ligation. Adapters comprising a complementary thymine overhang were then used to selectively ligate to and enrich for the blunt-ended termini resulting from cleavage by the DSB agent.

The NEBNext Ultra End Repair/dA-tailing module reagents (NEB, E7442L) were placed on ice (and allowed to thaw, if previously frozen). The 33 microliter end-repair reaction was assembled as follows: 27.7 microliters fragmented DNA (from Example 8), 3.3 microliters 10× end-repair reaction buffer, 1.5 microliters end-repair enzyme mix, and 0.5 microliters molecular biology grade water. The reaction was incubated for 30 minutes at 20 degrees Celsius, then incubated for 30 minutes at 65 degrees Celsius.

A 12 microliter solution of Adapter #2 (48 micromolar final concentration) was prepared according to the following: 1 microliter 100 micromolar HPLC-purified 5'-phosphorylated Adapter 2 N7 Forward (SEQ ID NO: 8), 1 microliter 100 micromolar HPLC-purified 5'-phosphorylated Adapter 2 N6 Forward (SEQ ID NO: 9), 1 microliter 100 micromolar HPLC-purified 5'-phosphorylated Adapter 2 N5 Forward (SEQ ID NO: 10), 3 microliters 100 micromolar Adapter 2 Reverse (SEQ ID NO: 11), and 6 microliters 2× annealing buffer (20 mM Tris pH 7.5 (prepared from Tris-HCl, pH 8.0 (Sigma Aldrich, T3038)), 100 mM NaCl (Sigma Aldrich, S5150), and 2 mM EDTA (Sigma-Aldrich, 03690-100ML)). The mixture was incubated for 5 minutes at 95 degrees Celsius, and allowed to cool to room temperature for approximately 45 minutes. The Adapter #2 oligos annealed to form a functional adapter.

The 41.75 microliter ligation reaction was assembled using the NEBNext® Ultra Ligation Module (NEB, E7445L) according to the following: 32.5 microliters end-repaired DNA (prepared as above), 1.25 microliters 12.5 micromolar Adapter #2 (prepared as above), 7.5 microliters Blunt/TA Ligase Master Mix (New England BioLabs), and 0.5 microliters Ligation Enhancer (New England BioLabs). The ligation reaction was incubated for one hour at 20 degrees Celsius.

The resulting adapter-ligated DNA may be purified according to Example 10.

Example 10: Affinity Purification with Streptavidin Beads

In this example, DNA fragments that had been ligated to biotinylated-Adapter #1 and Adapter #2 were affinity purified using Streptavidin beads.

2× Block and Wash (B&W) buffer for affinity purification was prepared as follows: 10 mM Tris, pH 7.5 ((prepared from Tris-HCl, pH 8.0 (Sigma Aldrich, T3038)), 2 M NaCl (prepared from Sigma Aldrich, S5150), and 1 mM EDTA (prepared from Sigma-Aldrich, 03690-100ML)).

Dynabeads® M-280 Streptavidin (Invitrogen 11206D, or Thermo-Fisher) were removed from storage at 4 degrees Celsius and mixed by gentle inversion. One volume (25 microliters per reaction) of Dynabeads® was mixed with 5 volumes (125 microliters) of 1× B&W buffer, prepared from the 2× B&W buffer described above. The washed Dynabeads® mixture was placed on a magnetic stand and allowed to pellet for approximately 5 minutes. The supernatant was removed. The Dynabeads® were washed, mixed, pelleted, and supernatant removed again. The washed beads were resuspended in 41 microliters of 2× B&W buffer, to which 41 microliters of adapter-ligated DNA (from Example 9) was added.

The bead/DNA mixture was allowed to incubate for 30 minutes at 20 degrees Celsius, with constant gentle inversion to ensure proper mixing. The samples were placed on a compatible magnetic stand. Beads were allowed to pellet for 5 minutes, and the supernatant was removed. The beads were washed two times by adding 200 microliters of 1× B&W buffer, allowed to incubate for 30 seconds each time, and the supernatant removed each time. A third wash was performed with 200 microliters of 10 mM Tris-HCl pH 8.5, incubated for 30 seconds, and supernatant removed. The sample was removed from the magnet. 20 microliters of 10 mM Tris-HCl pH 8.5 was added, and mixed with the beads by pipetting up and down several times.

The washed beads, comprising the purified DNA fragments, may be further processed according to Example 11 for PCR amplification of the DNA fragments.

Example 11: Recovery and Indexing PCR

In this example, the purified DNA fragments were amplified and indexed for Illumina sequencing.

A 50 microliter polymerase chain reaction (PCR) reaction was assembled according to the following: 22.5 microliters bead mixture (prepared according to Example 10), 2.5 microliters 10 micromolar Recovery PCR Forward (SEQ ID NO: 12), 2.5 microliters 10 micromolar Recovery PCR Reverse (SEQ ID NO: 13), 22.5 microliters Q5 Hot-Start 2× Master Mix (NEB, M0494L).

The PCR reaction mixture was placed in a thermal cycler with the following program:
1. 98 degrees Celsius for 2 minutes
2. 98 degrees Celsius for 10 seconds
3. 61 degrees Celsius for 30 seconds
4. 72 degrees Celsius for 2 minutes
Steps 2-4 were repeated 11 times, for a total of 12 cycles
5. 72 degrees Celsius for 2 minutes
6. Hold at 4 degrees Celsius (optional, if the PCR reaction was not removed immediately after the cycler ends)

The PCR reaction mixture was removed from the thermal cycler, placed on a compatible stand, and the beads allowed to pellet for 5 minutes. 30 microliters of supernatant were removed to a fresh tube. Optionally, the supernatant was diluted by adding 3 microliters of recovery PCR product to 147.5 microliters of microbiology grade water.

A 40 microliter Indexing PCR reaction was set up according to the following: 12 microliters of recovery PCR DNA (prepared as above), 4 microliters 2.5 micromolar Index Primer Forward (SEQ ID NO: 14), 4 microliters 2.5 micromolar Index Primer Reverse (SEQ ID NO: 15), 20 microliters Q5 2× Master Mix (NEB, M0494L), wherein N's denote Index sequences.

The Indexing PCR reaction mixture was placed in a thermal cycler with the following program:
1. 98 degrees Celsius for 2 minutes
2. 98 degrees Celsius for 10 seconds
3. 60 degrees Celsius for 30 seconds
4. 72 degrees Celsius for 2 minutes
Steps 2-4 were repeated 13 times, for a total of 14 cycles
5. 72 degrees Celsius for 2 minutes
6. Hold at 4 degrees Celsius (optional, if the PCR reaction was not removed immediately after the cycler ends)

All samples from the Indexing PCR step were pooled, for a total of 20-1000 microliters.

Example 12: Pool Cleanup

The pooled samples from the Indexing PCR reaction of Example 11 were cleaned. 0.7× volume of SPRIselect reagent or AMPure beads was added to the pooled sample, and mixed well by pipetting up and down. The reaction mixture was incubated for 5 minutes at room temperature. The reaction tube was placed on a magnetic stand, and the beads allowed to pellet for 5 minutes. The supernatant was removed, and the beads washed two times for 30 seconds each time, with 1 mL freshly prepared 85% ethanol. The ethanol was allowed to evaporate for 10-15 minutes each time. The tube was removed from the magnetic stand, and 1 volume of water was added. The reaction was mixed by pipetting up and down several times. The reaction mixture was incubated for 10 minutes at room temperature. The reaction tube was placed on the magnetic stand, and the beads allowed to pellet for 5 minutes. The supernatant was removed, and replaced with 0.95× volume of molecular biology grade water or 20 microliters of 10 mM Tris-HCl pH 8.5. The library was optionally stored at −20 degrees Celsius prior to library quantification and sequencing.

Example 13: Library Quality Control

Library QC may be performed by any method known in the art. This example describes one exemplary method.

The library prepared according to Example 12 was analyzed to ensure that no detectable adapter dimers (approximately 180 bp) were present, and that large (greater than 1000 bp) fragments were minimized. The library was diluted 1:10 and 1:5 by volume in molecular biology grade water, and loaded onto an Agilent Bioanalyzer High Sensitivity DNA Chip.

If the size range was too large (more than 25% of library above 1,000 bp) a 0.5× right-side SPRI cleanup was performed to adjust the size range. Fragments larger than 1,000 bp could alter quantification results but would not cluster on the sequencing flow cell. The cleanup protocol was performed as follows.

0.5× volume of SPRIselect reagent was added to the pooled sample, and mixed well by pipetting up and down. The reaction mixture was incubated at room temperature for 5 minutes, and placed on a magnetic stand. The beads were allowed to pellet for 5 minutes, and the supernatant was removed, and beads transferred to a fresh tube. 1.2× volumes of SPRIselect reagent was added, and incubated, pelleted, and supernatant removed as previously described. The beads were washed two times for 30 seconds each time, with 1 mL freshly prepared 85% ethanol. The ethanol was allowed to evaporate for 10-15 minutes, until the beads were dry. The reaction plate was removed from the magnetic stand, and 1 volume of water was added, mixing with the beads by pipetting up and down. The reaction mixture was incubated at room temperature for 10 minutes. The sample was placed back on the magnetic stand, and the beads allowed to pellet for 5 minutes. The supernatant was removed, the beads transferred to a new tube, and 0.9× volume of molecular biology grade water was added. If necessary, the pool cleanup of Example 12 may be performed again to remove any residual adapter dimer/small fragments from the library.

Example 14: Library Quantification and Sequencing

Library quantification may be performed by any method known in the art. In this example, library quantification was performed using qPCR or Qubit 3.0. Sequencing depth depends upon library quality and the specific application. In this example, 2-3 million reads (150 bp, single-end) per sample was performed, using an Illumina MiSeq or HiSeq.

Example 15: Double-Strand Break Identification and Characterization

The cleaved DNA that was tagged, enriched, and sequenced according to Examples 1-14 were then mapped to a corresponding reference genome. In the resulting alignments, sites cleaved by the DSB agent, for example the Cas9 endonuclease-sgRNA ribonucleoprotein (RNP) complex, yielded sequence read pileups that terminated at the cut site, approximately 3 nucleotides proximal to the Protospacer Adjacent Motif (PAM) sequence.

At least fourteen DSB recognition and cleavage sites were identified, as described in FIG. 5A: one target site (Site ID 1, Chromosome 2 nucleotide positions 4233973-4233995, given as SEQ ID NO: 16) and fourteen off-target sites (SEQ ID NOs: 17-29).

All fourteen sites comprised the canonical Cas9 PAM recognition sequence "NGG", as described in FIG. 5B, with the target recognition site comprising the PAM sequence "AGG".

FIG. 6 shows that the method provided herein resulted in higher read counts at double-strand break sites as compared to the control method lacking the phosphatase treatment. As shown in FIG. 7, phosphatase treatment of resulted in an approximately 8-fold improvement of double-strand-break site reads (target and off-target cleavage sites) than a control method lacking the phosphatase treatment.

Example 16: Method for the Identification and Characterization of a Double-Strand Break In this method, an alternative approach for the identification and characterization of a double-strand break produced by a double-strand-break-inducing agent capable of effecting a "blunt-end" cut in a double-stranded polynucleotide is provided.

The following materials, reagents, and equipment were used, provided herein solely as examples, with substitutions and variations according to practices in the art understood: Thermal Cycler vapo.protect (Eppendorf), Rotor Gene 6000 Real-Time PCR Machine (Corbett), Nanodrop Spectrophotometer 1000 (Thermo Scientific), Fluorometer Qubit (Invitrogen), Covaris M220 Focused-ultrasonicator (Covaris), Concentrator 5301 (Eppendorf), 16-tube DynaMag-2 Magnetic Rack (Invitrogen, 12321D), Tube Centrifuge 5415 R (Eppendorf), Transilluminator Biometra Ti5 (Biometra), Personal Spin-Vortex Microspin FV-2400 (Biosan), HU13 Midi Horizontal Submarine Gel Electrophoresis System (Abdos Labware), Standard set of manual pipettes (2, 20, 200, 1000 ul and multi-channel if necessary), 2100 Electrophoresis Bioanalyzer (Agilent), Illumina Sequencing Machine (MySeq, NextSeq, HiSeq), 10 ul/20 ul/200 ul/1000 ul standard tips, 2 ul/10 ul/20 ul/200 ul/1000 ul filter tips (DNase/RNase free), 1-200 ul Clear Wide Bore Maxymum Recovery tips (Axygen, T-205-WB-C-L), Microcentrifuge Tubes 1.5 mL, DNA LoBind Tubes 1.5 mL (Eppendorf, 0030 108.051) 0.1 mL 4-Strip Rotor-Gene Style Tubes and Caps (Starlab, 11402-0400), Reaction Tubes 0.5 mL (Greiner bio-one, 667201), Centrifuge Tubes, Conical, 15 mL and 50 mL, 0.2 ml 8-strip PCR tubes with individual caps, microTUBE AFA Fiber Pre-Slit Snap-Cap 6×16 mm (Covaris, 520045), FastAP Thermosensitive Alkaline Phosphatase (1 U/µL) (Thermo Scientific, EF0654), T4 DNA Ligase (5 U/µL) (Thermo Scientific, EL0014), DreamTaq DNA Polymerase (5 U/µL) (Thermo Scientific, EP0702), FastDigest NotI (Thermo Scientific, FD0594), Lambda Exonuclease (10 U/µL) (Thermo Scientific, EN0561), T4 DNA Polymerase (5 U/µL) (Thermo Scientific, EP0061), MagJET NGS Cleanup and Size Selection Kit (Thermo Scientific, K2828), Columns from EpiJET Bisulfite Conversion Kit (Thermo Scientific, K1461), EDTA (0.5M), pH8.0 (Thermo Scientific, R1021), ATP Solution (100 mM) (Thermo Scientific, R0441), dNTP Mix (10 mM each) (Thermo Scientific, R0191), 50% (w/v) PEG 4000 solution from T4 DNA Ligase, 5 Weiss U/µL (Thermo Scientific, EL0014), 50% (w/v) PEG 8000 solution (Thermo Scientific, EL0014), Taq Buffer with $(NH4)_2SO_4$ (10×) (Thermo Scientific, B33), Triton X-100 for molecular biology (Sigma-Aldrich, T8787-50ML), FastDigest Buffer (10×) (Thermo Scientific, B64), SYBR Green I 10,000× in DMSO (Sigma Aldrich, S9430), Tris (Carl-Roth, 5429.1), EDTA (Carl-Roth, 8043.3), NaCl (Carl-Roth, 9265.1), KOH (Carl-Roth, 5658.1), HCl (Carl-Roth, 4625.1), Acetic acid (Carl-Roth, 3738.1), Glycine (Carl-Roth, 3187.1), Magnesium acetate tetrahydrate (Carl-Roth, 0275.1), $MgCl_2$ (Carl-Roth, KK36.1), NaOH (Carl-Roth, 9356.1), Tween 20 (Carl-Roth, 9127.1), Agilent High Sensitivity DNA BioAnalayzer Kit, Qubit dsDNA HS Assay Kit (Thermo Scientific, Q32851), 2-propanol (Carl-Roth, 7343.2), Ethanol 96% (Carl-Roth, P075.1), Glycerol (Fisher Scientific, BP229-4), MilliQ purified water, PCR Add-on Kit for Illumina (Lexogen, SKU: 020.96), Purification Module with Magnetic Beads (Lexogen, SKU: 022.96), i7 Index Plate for QuantSeq/SENSE for Illumina (7001-7096) (Lexogen, SKU: 044.96).

As depicted in FIGS. 4A and 4B, first high molecular weight (HMW) genomic DNA (a cleavage target is colored cyan) was treated with a phosphatase to remove possible phosphate groups from the 5' DNA fragment ends (step C). After DNA digestion with the DSB agent or RNP complex (step D) a modified adapter containing biotin (indicated as "bio") at the 5' end and phosphorothioate bonds (shown as a circle) was ligated to the blunt DNA ends bearing 5'-phosphate group (indicated as "P")(step E). Nick removal (step F) using Taq DNA polymerase (possesses strand displacement activity) reconstituted a recognition site of the restriction endonuclease NotI. After DNA shearing (step G) DNA was purified to remove an excess of unligated adapter (step H). Biotinylated DNA fragments were captured by streptavidin coated magnetic beads (step I), then the DNA fragments were released from the beads by NotI cleavage (step J). The bottom DNA strand was degraded using lambda exonuclease (step K), and ssDNA was purified (step L). After synthesis of the second DNA strand (step M) using a random primer (colored green) the library was amplified and barcoded (step P), then it was purified and size-selected (step Q). The obtained DNA fragments comprised Illumina sequences (P7 and P5, respectively) and i7 indices.

The method is described in detail as follows.

Annealing of the Adapter

The adapter (20 uM) was prepared by annealing of its upper and bottom strands (ratio 1:1) in Annealing buffer (6.6 mM Tris-acetate (pH7.0 at 25° C.), 13.2 mM K-acetate).

Assembly of RNP Complex

The 2×RNP complex was assembled by mixing Cas9 (SEQ ID NO:1, final concentration 2 uM) and sgRNA (final concentration 4 uM) (keeping a guide RNA:Cas9 ratio of at least 2:1) in Assembly Buffer (10 mM Tris-HCl (pH7.5 at 25° C.), 100 mM NaCl, 1 mM DTT, 1 mM EDTA) and incubation at 37° C. for 1 hr.

1M $MgCl_2$ was added to the final concentration of 16 mM.

If serial dilutions of the RNP complex were used then the initially assembled RNP complex was diluted with the 1× mix of Assembly Buffer, Cas9 Storage Buffer (10 mM Tris-HCl (pH7.5 at 25° C.), 100 mM NaCl, 1 mM DTT, 1 mM EDTA, 50% glycerol (v/v)) and $MgCl_2$ maintaining the same buffer composition.

Treatment of Genomic DNA with FastAP (FIG. 4A Step C)

3 ug of HMW gDNA (concentration determined using Qubit) was used for one experiment. If more experiments were planned, a master mix was prepared, and 20 ul of the master mix was dispensed into individual 0.2 ml PCR tubes. Wide bore tips and gentle pipetting was utilized to avoid gDNA mechanical shearing.

The treatment with FastAP resulted in removing of a phosphate group form the 5' end of gDNA fragments.

The following reaction was assembled and mixed gently by pipetting, then incubated at 37° C. for 1 hr, then 80° C. for 20 min.:

| gDNA | Xul (3 ug) |
|---|---|
| FastAP buffer (10x) | 2 ul |
| FastAP (1 U/ul) | 1 ul |
| Water | to 20 ul |
| Total | 20 ul |

Digestion of FastAP Treated gDNA with RNP Complex 20 ul of RNP complex (2×) was added to 20 ul of FastAP treated gDNA (total 40 ul), and mixed gently by pipetting, then incubating, the sample at 37° C. for 1 hr, then 80° C. for 20 min.

Adapter Ligation (FIG. 4A Step E)

The following components were added to the Cas9 digested gDNA (if more experiments were planned, a master mix was prepared, then 40 ul of the master mix was dispensed into individual samples). The sample was mixed gently by pipetting, then incubated at 22° C. for 1 hr, then 80° C. for 20 min.

| Adapter (20 uM) | 4 ul |
|---|---|
| DTT (1M) | 0.8 ul |
| Mg-acetate (100 mM) | 4 ul |
| ATP (100 mM) | 0.4 ul |
| PEG 4000 (50% w/v) | 6 ul |
| T4 DNA ligase (5 U/ul) | 4 ul |
| Tris-HCl (200 mM, pH 8.0 at 25° C.) | 1 ul |
| Water | 19.8 ul |
| Total | 80 ul |

Wherein the adapters for the present experiment were:

```
Adapter upper strand (comprising SEQ ID NO: 30):
5'-Biotin-AGTTACGCAACCGAGACGCGGCCGCsGsTsGs
ACTGGAGTTCAGACGTGTGCTCTTCCGATCT-3'
where "s" stands for PTO modification Adapter bottom strand (comprising SEQ ID NO: 31):
5' AGATCGGAAGAGCACACGTCTGAACTCCAGTCACGCCCGGGCGTCT
CGGTTGCddC-3'
```

Nick Removal (FIG. 4A Step F)

The following components were added to the ligated gDNA (if more experiments were planned, a master mix was prepared, and 20 ul of the master mix was dispensed into individual samples)

| Taq Buffer with $(NH_4)_2SO_4$ (10X) | 10 ul |
|---|---|
| dNTP Mix (10 mM each) | 2 ul |
| EDTA (0.5M) | 0.8 ul |
| DreamTaq DNA Pol. (5 U/uL) | 2 ul |
| Water | 5.2 ul |
| Total | 100 ul |

The reaction was mixed by pipetting, then incubated at 72° C. for 15 min. 5 ul of EDTA (0.5M) was then added.

DNA Shearing (FIG. 4A Step G)

The sample was transferred into a microTUBE AFA Fiber Pre-Slit Snap-Cap 6×16 mm. DNA with sheared with a Covaris M220 Focused-ultrasonicator using following parameters:

| Peak Incident Power (W) | 50 |
|---|---|
| Duty Factor (%) | 20 |
| Cycles per Burst | 200 |
| Treatment Time (s) | 200 |
| Temperature (° C.) | 20 |

Adapter Removal (FIG. 4B Step H)

DNA was purified using a MagJET NGS Cleanup and Size Selection Kit according to manufacturer recommendations (cleanup protocol). To avoid precipitates, a fresh Binding Mix was prepared before each use. The exact amount of 100% isopropanol was added to a final concentration of 36% (v/v) (see product information for the guidelines): isopropanol was first added, then add Binding Buffer. The solution was mixed well by inverting tube several times, shaking or vortexing. Binding Mix was prepared and used within 24 hours. Before each use, MagJET Magnetic Beads were mixed thoroughly to fully resuspend the particles in the storage solution.

5 uL of MagJET Magnetic Beads was mixed with 700 uL of Binding Mix.

Exactly 100 uL DNA sample was transferred to a microcentrifuge tube with pre-mixed MagJET Magnetic Beads and Binding Mix.

The total reaction volume was mixed by vortexing until a homogenous suspension was obtained, and the tube was pulsed-spun to collect all the drops, and then incubated at room temperature for 5 minutes.

The tube was briefly spun down to collect droplets, and placed in the magnetic rack for 2-3 minutes or until the beads formed a tight pellet. Keeping the reaction vessel on the magnet, the supernatant was carefully removed and discarded by using a pipette, ensuring that all supernatant was removed. If the pellet of magnetic particles was disturbed, the sample was mixed and beads allowed to settle to the magnet again.

400 uL of Wash Solution (supplemented with ethanol) was added, and mixed by vortexing, and placed it back in the magnetic rack for 1-2 minutes. When solution cleared, the supernatant was carefully removed and discarded by using a pipette. This step was then repeated.

To remove residual Wash Solution, the tube was pulsed-spun, and placed back in the magnetic rack for 1 minute, and any remaining supernatant was carefully removed with a pipette without disturbing the pellet.

Keeping the tube on the magnet, the magnetic particles were allowed to air dry at room temperature for 5 minutes or until there were no droplets of Wash Solution left on the walls of the tube.

The tube was removed from the magnet and 50 uL of Elution Buffer was added.

The tube was mixed by vortexing, and spun down to collect all the drops and then incubated at room temperature for 1 minute.

The tube was then pulse-spun to collect droplets. The tube was placed in the magnetic rack for 2-3 minutes or until the beads formed a tight pellet. Without removing the microcentrifuge tube from the magnetic rack, the eluate was removed and transferred to a storage tube. Note: If the pellet of magnetic particles was disturbed or eluate is not clear enough, the sample was mixed by gentle pipetting and allowing the beads settle to the magnet again.

Affinity Purification with Streptavidin Beads (FIG. 4B Step I)

2× Wash Buffer for the Dynabead affinity purification procedure was prepared as follows: 10 mM Tris-HCl (pH8.0 at 25° C.), 2M NaCl, 1 mM EDTA with and without 0.1% Tween 20.

The Dynabeads were removed from 4° C., and mixed by gently inverting the tube.

One volume (25 ul per reaction) of the Dynabeads was mixed with one volume (25 ul) of 2× Wash Buffer with Tween 20.

The Dynabead mixture was placed on a magnetic stand, and allowed time to pellet (~5 min), remove supernatant.

Beads were resuspended in 50 ul of Wash Buffer with Tween 20.

50 ul of the prepared Dynabeads was mixed with 50 ul of the eluted DNA (from step H). The bead/DNA mixture was allowed to rotate for 30 minutes at RT, with gentle inversion, ensuring that the beads were mixing.

After incubation, samples were placed on a compatible magnetic stand, and allowed to pellet for 5 minutes. The supernatant was then removed.

The beads were mixed by adding 100 ul of 1× Wash Buffer with Tween 20, allowing to incubate for 30 seconds. Beads were allowed to pellet for 5 minutes using a magnetic stand, and the supernatant then removed. This step was repeated three times: first, using 1× Wash Buffer with Tween 20, then using 1× Wash Buffer without Tween 20, and finally 1× FastDigest Buffer (10× FastDigest Buffer is supplied with FD NotI).

The sample was removed from the magnet, and 25 ul of 1× FastDigest Buffer was added. and mixed by vortexing.

DNA Cleavage with NotI (FIG. 4B Step J)

1 ul of FD NotI was added, mixed by pipetting, then incubated at 37° C. for 30 min with occasional mixing.

Beads were allowed to pellet using a magnetic stand for 5 minutes, then the supernatant was collected.

DNA Digestion with Lambda Exonuclease (FIG. 4B Step K)

10× Reaction Buffer was prepared: 670 mM glycine-KOH (pH9.4 at 25° C.), 0.1% Triton X-100.

The following components were added to the supernatant from step J (if more experiments ere planned, a master mix was prepared, and 95 ul of the master mix was dispensed into individual samples):

| | |
|---|---|
| 10X Reaction Buffer | 9.5 ul |
| Lambda Exonuclease (10 U/uL) | 2 ul |
| Water | 83.5 ul |
| Total | 120 ul |

The reaction was mixed by pipetting, then incubated at 37° C. for 1 hr. The reaction was then incubated at 80° C. for 20 min.

ssDNA Purification Using EpiJET Bisulfite Conversion Kit (FIG. 4B Step L)

400 ul of Binding buffer was added to the spin column.

120 ul of the sample (from K step) was added to the spin column preloaded with Binding Buffer.

The solutions were mixed by pipetting inside the column.

The solution was spun at 14000×g for 30 s, and the flowthrough discarded.

200 ul of 1× Wash buffer was added, and the sample spun at 14000×g for 30 s, and the flowthrough discarded.

200 ul of 1× Wash buffer was added, and the sample spun at 14000×g for 60 s, and the flowthrough discarded.

10 ul of water was added, and the sample spun at 14000×g for 60 s. This step was repeated with additional 10 ul of water, and the flowthrough (total 20 ul) with purified ssDNA was collected.

Synthesis of the Second Strand of DNA (FIG. 4B Step M)

The following components were added to the flowthrough from step L (if more experiments were planned, a master mix was prepared, then 25.5 ul of the master mix was dispensed into individual samples)

| | |
|---|---|
| 5X T4 DNA Polymerase Buffer | 10 ul |
| Magnesium acetate (100 mM) | 1.7 ul |
| PEG 8000 (50% (w/v)) | 8 ul |
| Second strand synthesis primer (1.25 uM) | 5 ul |
| Total | 45.5 ul |

Where the second strand synthesis primer is given as SEQ ID NO:32 for the present example:

5'-CCCTACACGACGCTCTTCCGATCTNNNNNNNNNNNNN-3'

The reaction was mixed by pipetting, then incubated for 1 minute at 98° C. in a thermocycler, and slowly cooled down to 25° C. by setting the ramp speed to 10% (0.5° C./second).

The reaction was incubated at 25° C. for 30 min.

3.5 ul of dNTP Mix (10 mM each) was added, then mixed by pipetting.

1 ul of T4 DNA Polymerase (5 U/uL) was added, then mixed by pipetting.

The reaction was incubated at 25° C. for 15 min.

DNA Purification Using Purification Module with Magnetic Beads (FIG. 4B Step N)

The Purification Beads (PB) equilibrated for 30 minutes at room temperature before use to ensure that any PB that may have settled was properly resuspended before adding them to the reaction.

20 ul of properly resuspended Purification Beads (PB) was added to each reaction, mixed well, and incubated for 5 minutes at room temperature.

The tube was placed in the magnetic rack, and the beads allowed to collect for 2-5 minutes or until the supernatant as completely clear (depending on the strength of the magnet).

The clear supernatant was removed and discarded without removing the tube from the magnetic rack, ensuring that accumulated beads were not disturbed.

40 ul of Elution Buffer (EB) was added, the plate removed from the magnet, and the beads resuspended properly in EB. The solution was incubated for 2 minutes at room temperature.

72 ul of Purification Solution (PS) was added to the beads/EB mix to re-precipitate the library, mixed thoroughly, and incubated for 5 minutes at room temperature.

The tube was placed into the magnetic rack, and the beads allowed to collect for 2-5 minutes or until the supernatant was completely clear.

The clear supernatant was removed and discarded without removing the tube from the magnetic rack, ensuring that accumulated beads were not disturbed.

120 ul of 80% EtOH was added, and the beads washed for 30 seconds. The tube was left in contact with the magnet so that the beads would not be resuspended during this washing step. The supernatant was removed and discarded. This washing step was repeated once for a total of two washes, ensuring complete removal of the supernatant as traces of ethanol could have inhibited subsequent PCR reactions.

The tube was left in contact with the magnet, and the beads allowed dry for 5-10 minutes or until all ethanol had evaporated. The beads were not allowed to dry for too long (appearance of visible cracks) as this would have negatively influenced the elution and the resulting library yield.

30 ul of Elution Buffer (EB) was added per well, the tube removed from the magnet, and beads properly resuspended in EB. The solution was incubated for 2 minutes at room temperature.

The tube was placed into a magnetic rack and the beads allowed to collect for 2-5 minutes or until the supernatant was completely clear.

The clear supernatant was transferred into a new tube.

qPCR to Determine the Exact Cycle Number for Library Amplification

For determining the cycle number for library amplification, the PCR Add-on Kit for Illumina was used.

A PCR Reaction was assembled according to the following (if more experiments were planned, a master mix was prepared, then 8.7 ul of the master mix was dispensed into individual samples):

| | |
|---|---|
| The supernatant from N step | 11.3 ul |
| PCR mix (PCR) | 4.63 ul |
| Enzyme mix (E) | 0.67 ul |
| Amplification primer (7000) | 3.3 ul |
| 20X SYBR Green I solution (diluted in DMSO) | 0.15 ul |
| Total | 20 ul |

A RT-cycler was used to carry out the following PCR program:
1. 98° C. for 2 min
2. 98° C. for 10 s
3. 65° C. for 20 s
4. 72° C. for 30 s
5. Repeat Steps 2-4 30 times
6. 72° C. for 2 min Note: SYBR Green I has an emission maximum at 520 nm, which for some qPCR machines had to be adjusted manually.

The maximum fluorescence value at which the fluorescence reaches a plateau was determined. The fluorescence at 33% of the maximum was calculated, and the corresponding cycle number was used for the endpoint PCR with the remaining template.

Library Amplification and Barcoding (FIG. 4B Step P)

For library amplification and barcoding, the PCR Add-on Kit for Illumina and i7 Index Plate for QuantSeq/SENSE for Illumina (7001-7096) were used.

A PCR Reaction was assembled according to the following (if more experiments were planned, a master mix was prepared, then 13 ul of the master mix was dispensed into individual samples):

| | |
|---|---|
| The supernatant from N step | 17 ul |
| PCR mix (PCR) | 7 ul |
| Enzyme mix (E) | 1 ul |
| Barcode primer | 5 ul |
| Total | 30 ul |

A thermal cycler was used to carry out the following PCR program:
1. 98° C. for 2 min
2. 98° C. for 10 s
3. 65° C. for 20 s
4. 72° C. for 30 s 5. Repeat steps 2-4 using the cycle number determined in 0 step
6. 72° C. for 2 min
7. Hold at 4° C.

DNA Purification and Size Selection using Purification Module with Magnetic Beads (FIG. 4B Step Q)

The Purification Beads (PB) equilibrated for 30 minutes at room temperature before use, ensuring that any PB that may have settled and were properly resuspended before adding them to the reaction.

30 ul of properly resuspended Purification Beads (PB) was added to each reaction, mixed well, and allowed incubate for 5 minutes at room temperature.

The tube was placed in the magnetic rack, and beads allowed collect for 2-5 minutes or until the supernatant as completely clear (depending on the strength of the magnet).

The clear supernatant was removed and discarded, without removing the tube from the magnetic rack, ensuring that the accumulated beads were not disturbed.

30 ul of Elution Buffer (EB) was added, the plate removed from the magnet, and the beads properly resuspended in EB. The sample was incubated for 2 minutes at room temperature.

30 ul of Purification Solution (PS) was added to the beads/EB mix to re-precipitate the library, mixed thoroughly, and incubated for 5 minutes at room temperature.

The tube was placed into the magnetic rack, and the beads allowed collect for 2-5 minutes or until the supernatant was completely clear.

The clear supernatant was removed and discarded without removing the tube from the magnetic rack, ensuring that the accumulated beads were not disturbed.

120 ul of 80% EtOH was added, and the beads washed for 30 seconds. The tube was left in contact with the magnet to prevent beads from resuspending during this washing step. The supernatant was removed and discarded. This washing step was repeated once for a total of two washes, ensuring that supernatant completely removed traces of ethanol that would inhibit subsequent PCR reactions.

The tube was left in contact with the magnet, and beads allowed to dry for 5-10 minutes or until all ethanol has evaporated. The beads were not allowed to dry for too long (appearance of visible cracks) as this would have negatively influenced the elution and the resulting library yield.

20 ul of Elution Buffer (EB) was added per well, the tube removed from the magnet, the beads properly resuspended in EB. The sample was incubated for 2 minutes at room temperature.

The tube was placed into a magnetic rack and beads allowed to collect for 2-5 minutes or until the supernatant was completely clear.

The clear supernatant was transferred into a new tube.

Library Quantification and Quality Control

For library quantification by fluorimeter, Qubit and Qubit dsDNA HS Assay Kit was used with 1 ul of the supernatant (from Step Q). For library quality control, 1 ul of the supernatant (from Step Q) was loaded on an Agilent Bioanalyzer High Sensitivity DNA chip.

Double-strand break identification and characterization was performed essentially as described in Example 15.

Results

Several experimental strategies were tested. Strategies I, II, and III utilized high molecular weight (HMW) genomic DNA; Strategy IV utilized a library that was generated using sheared genomic DNA (500-800 bp). Various blocking adapters were examined as methods to decrease the background noise of the assay: the 1$^{st}$ blocking adapter was a simple double-stranded adapter. Y-shaped adapters were based on Illumina designs. U-shaped adapters were hairpin-like sequences that fold back on themselves leaving only one exposed double stranded 5' and 3' end. As shown in Table 1, a phosphatase treatment as a means to block random/background adapter ligation worked the best.

TABLE 1

| Sample | Total Mapped Reads | Site-Mapped Reads | On-Target Share of Total Reads |
| --- | --- | --- | --- |
| Strategy I no blocking adapters (no Cas9) | 3,086,465 | 8 | 0.00% |
| Strategy I no blocking adapters | 3,445,754 | 2433 | 0.07% |
| Strategy I with blocking adapters (no Cas9) | 893,782 | 1 | 0.00% |
| Strategy I with blocking adapters | 2,084,930 | 1657 | 0.08% |
| Strategy II with blocking adapters | 540,948 | 12 | 0.00% |
| Strategy III with blocking adapters | 59,833 | 2 | 0.00% |
| Strategy I with blocking adapters (no Cas9; no gRNA) | 3,429,156 | 84 | 0.0024% |
| Strategy I with blocking adapters (no gRNA) | 3,742,596 | 98 | 0.0026% |
| Strategy I with blocking adapters (no Cas9) | 4,539,303 | 84 | 0.0019% |
| Strategy I with blocking adapters | 3,471,144 | 45,537 | 1.3119% |
| Strategy I with blocking adapters and nuclease | 4,856,164 | 126,337 | 2.6016% |
| Strategy I no blocking adapters | 3,699,331 | 26,841 | 0.7256% |
| Strategy I with phosphatase | 4,676,620 | 225,840 | 4.8291% |
| Strategy IV with blocking "Y" adapters (no Cas9; no gRNA) | 5,843,406 | 76 | 0.0013% |
| Strategy IV with blocking "Y" adapters (no gRNA) | 3,587,796 | 1,481 | 0.0413% |
| Strategy IV with blocking "U" adapters (no Cas9; no gRNA) | 4,315,693 | 50 | 0.0012% |
| Strategy IV with blocking "U" adapters (no gRNA) | 3,404,986 | 1,485 | 0.0436% |
| Strategy IV with blocking "U" adapters and nuclease | 1,637,692 | 39,971 | 2.4407% |
| Strategy IV no treatment | 4,084,096 | 3,149 | 0.0771% |
| Strategy IV with phosphatase | 4,964,416 | 57,795 | 1.1642% |
| Strategy IV with phosphatase and dA addition | 2,650,412 | 62,871 | 2.3721% |

Example 17: Comparison of In-Vitro-Identified Double Strand Breaks with In-Vivo-Identified Double-Strand-Break-Inducing-Agent Cleavage Sites In some aspects, the target and/or off-target cleavage sites identified from the in vitro methods provided herein may be compared to the double-strand breaks identified from an in vivo method, such as molecular inversion probes sequencing (MIPs).

In some aspects, the sequence information of the target and/or off-target cleavage sites identified from the in vitro methods provided herein (in one aspect, as described in Examples 1-15) may be used to design the targeting arm probe sequences for MIPs.

Use of MIP technology allows for the detection of changes at the single nucleotide level without prior knowledge of the exact edit that is generated at each site. The MIPs technology may be used to characterize both the region of desired editing as well as potential off-target locations in the genome that may also exhibit editing as a result of DSB agent activity.

A sample of genomic DNA with one or more site(s) of interest (comprising target or off-target cleavage site(s)) is selected, and an approximately 100-base pair window comprising each site of interest is analyzed (FIG. 8 Step A).

Molecular probe "targeting arms" are designed to complement sequences within each window that are within 70 bp of the site of interest, comprise 17-28 base pairs, and have a predicted melting temperature of 68-72 degrees Celsius (FIG. 8 Step B, with the "targeting arms" depicted as heavy lines). The two targeting arms for each site are linked with a 30-50 bp common backbone sequence (depicted as a dashed line in FIG. 8 Step B), and ordered as individual oligos with a 5' phosphorylation. The sets of targeting arms plus linker circularized and pooled (FIG. 8 Step C), and introduced to double-stranded DNA. The reaction is allowed to denature and incubate (FIG. 8 Step D). Following incubation, the hybridized MIPs are recircularized, and treated with exonuclease to remove linear genomic DNA and uncircularized probes (FIG. 8 Step E). The hybridized MIPs and target sequences are indexed and amplified. The amplicons are pooled and purified, and sequenced. The sequence of each of amplicons is assessed, from which the sequences of the sites of interest between the targeting arm sequences are determined (FIG. 8 Step F) and characterized.

Example 18: Use of Molecular Indexes to Infer In Vitro on and Off-Target Cleavage Efficiency In some aspects, the cleavage efficiencies of the target and/or off-target cleavage sites identified from the in vitro methods provided herein may be inferred by calculating the number of unique index sequences ligated to the double-strand break (DSB).

In some aspects, the inferred cleavage efficiency may be used to predict the probability of in vivo DSB formation and cellular repair.

In some aspects, the inferred cleavage efficiency may be used to select in vivo on- and off-targets targets for evaluating the evidence of DSB formation and cellular repair.

In some aspects, the inferred cleavage efficiency may be used to select targets with high on-target and low off-target probabilities.

Unique molecular identifiers (UMIs) also termed molecular indexes and Random Molecular Tags (RMTs) are a collection of random or semi-random sequences used to tag molecules prior to library construction and amplification (Fu, G. et al. (2014) Proc. Natl. Acad. Sci. USA. 111:1891-1896). Their purpose is to remove redundancy introduced by library amplification (for example but not limiting to the polymerase chain reaction (PCR)). For the methods described herein, they may be incorporated into the adapter sequences first ligated to the target sequence(s) cleaved in vitro by the DSB inducing reagent (FIG. 1 "Adapter 1", FIG. 2 "Adapter 1", FIG. 3 "Adapter 1", FIG. 4A step E), thereby providing a method to quantitate cleavage frequency. For example, if two reads align to a cleaved target sequence and each have the same UMI, then it is highly probable that they are duplicates generated by PCR or sequencing. Then by collapsing duplicates in the dataset, an accurate estimate of the concentration of the fragments in the initial in vitro reaction may be calculated.

---

We claim:

1. A method for characterizing a double-strand-break-inducing agent cleavage site of an isolated, purified polynucleotide, comprising:
   (a) adding phosphatase to the isolated, purified polynucleotide,
   (b) contacting the phosphatase-treated polynucleotide from (a) with a double-strand-break-inducing agent to create a library of polynucleotides,
   (c) optionally adding an adenine to the 3' ends of the polynucleotides of the library, and
   (d) ligating an adapter to the polynucleotides of the library, wherein the adapter comprises a nucleotide that is complementary to a terminal unpaired nucleotide of the polynucleotides of (b) or (c);
   further comprising sequencing said library of polynucleotides, identifying at least one double-strand-break site, and assessing at least one qualitative characteristic or quantitative characteristic; wherein the phosphatase addition results in an increased number of double-strand-break sequence reads compared to a control method not comprising the addition of phosphatase.

2. The method of claim 1, wherein the sequences of the polynucleotides of the last library are compared to the sequence(s) of at least one reference polynucleotide or genome.

3. The method of claim 1, wherein the polynucleotide is selected from the group consisting of: cDNA, plasmid DNA, genomic DNA, and synthetic DNA.

4. The method of claim 1, wherein the polynucleotide is linear.

5. The method of claim 1, wherein the polynucleotide is circularized.

6. The method of claim 1, wherein the first adapter is non-phosphorylated.

7. The method of claim 1, wherein the polynucleotide is obtained from a cell.

8. The method of claim 7, wherein the cell is a prokaryotic cell or a eukaryotic cell.

9. The method of claim 7, wherein said cell is transgenic.

10. The method of claim 7, wherein the eukaryotic cell is selected from the group consisting of: animal, plant, and fungus.

11. The method of claim 10, wherein the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell.

12. The method of claim 10, wherein the plant cell is selected from the group consisting of: Arabidposis, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp.

13. The method of claim 1, wherein the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain.

14. The method of claim 11, wherein the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a deactivated Cas endonuclease, and a functional fragment or functional variant of any of the preceding.

15. The method of claim 1, wherein the polynucleotide library generated in the fragmenting/shearing step comprises polynucleotide molecules between 100 and 1000 nucleotides in length.

16. The method of claim 1, wherein the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site.

17. The method of claim 16, wherein any of the polynucleotide compositions comprise a polynucleotide of interest selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide.

18. The method of claim 1, wherein the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a non-coding regulatory element, a marker, a complex trait locus, a QTL, and a heterologous polynucleotide.

19. The method of claim 1, wherein a characteristic of the double-strand-break-inducing agent is additionally determined.

20. The method of claim 19, wherein the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent.

21. The method of claim 1, wherein the value of said characteristic is compared to the value of the same characteristic of, or produced by, a reference double-strand-break-inducing agent.

22. The method of claim 21, wherein said value is increased as compared to that of the reference double-strand-break-inducing agent.

23. The method of claim 21, wherein said value is decreased as compared to that of the reference double-strand-break-inducing agent.

24. The method of claim 21, wherein said value is used to optimize a characteristic of a double-strand-break-inducing agent functional association.

25. The method of claim 24, wherein the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex.

26. The method of claim 1, wherein the cleavage site is a target cleavage site.

27. The method of claim 1, wherein the cleavage site is an off-target cleavage site.

28. The method of claim 1, wherein the double-strand-break-inducing agent of step (b) comprises a ribonucleoprotein comprising a Cas endonuclease and a guide ribonucleotide.

29. The method of claim 28, wherein the concentration of the ribonucleoprotein is at least 0.25 nM.

30. The method of claim 28, wherein the ratio of guide RNA to Cas endonuclease is 3:1.

31. The method of claim 1, wherein a plurality of double-strand-break-inducing agents are evaluated in parallel.

32. A method for characterizing a double-strand-break-inducing agent cleavage site, comprising:
  (a) adding phosphatase to a sample of isolated, purified polynucleotide,
  (b) contacting the phosphatase-treated polynucleotide from (a) with the double-strand-break-inducing agent to create a first library of polynucleotides,
  (c) ligating a double-stranded first adapter to the polynucleotides of the first library to create a second library of polynucleotides, wherein one strand of said double-stranded first adapter comprises a molecule for the purification of the polynucleotide,
  (d) removing the nicks and reconstituting a restriction endonuclease site to create a third library of polynucleotides,
  (e) shearing the polynucleotides of the third library to create a fourth library of fragmented polynucleotides,
  (f) capturing the fragmented polynucleotides of the fourth library that comprise the ligated first adapter, (g) cleaving the captured fragmented polynucleotides with a restriction endonuclease capable of recognizing the site introduced in (d) to create a fifth library of polynucleotides, (h) Adding lambda exonuclease to the polynucleotides of the fifth library and to create a sixth library of single stranded polynucleotides, (i) synthesizing complementary strands to the single stranded polynucleotides of the sixth library to create a seventh library, (j) purifying, amplifying, and size-selecting the polynucleotides of the seventh library, (k) sequencing the polynucleotides of the seventh library, (l) identifying at least one double-strand-break site, and (m) assessing at least one qualitative or quantitative characteristic of said double-strand-break-inducing site;

wherein the phosphatase addition results in an increased number of double-strand-break sequence reads compared to a control method not comprising the addition of phosphatase.

33. The method of claim 32, wherein the sequences of the polynucleotides of the last library are compared to the sequence(s) of at least one reference polynucleotide or genome.

34. The method of claim 32, wherein the polynucleotide is selected from the group consisting of: cDNA, plasmid DNA, genomic DNA, and synthetic DNA.

35. The method of claim 32, wherein the polynucleotide is linear.

36. The method of claim 32, wherein the polynucleotide is circularized.

37. The method of claim 32, wherein the first adapter is non-phosphorylated.

38. The method of claim 32, wherein the polynucleotide is obtained from a cell.

39. The method of claim 38, wherein the cell is a prokaryotic cell or a eukaryotic cell.

40. The method of claim 38, wherein said cell is transgenic.

41. The method of claim 39, wherein the eukaryotic cell is selected from the group consisting of: animal, plant, and fungus.

42. The method of claim 41, wherein the animal cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cell RHP, and human nasopharyngeal tumor KB cell.

43. The method of claim 41, wherein the plant cell is selected from the group consisting of: Arabidposis, corn (*Zea mays*), *Brassica* spp. (e.g., *B. napus, B. rapa, B. juncea*), rice (*Oryza sativa*), wheat (*Triticum aestivum*), soybean (*Glycine max*), tobacco (*Nicotiana tabacum*), cotton (*Gossypium barbadense, Gossypium hirsutum*), sugar beets (*Beta vulgaris*), sugarcane (*Saccharum* spp.), and *Brachypodium* spp.

44. The method of claim 32, wherein the double-strand-break-inducing agent is selected from the group consisting of: a ribonucleoprotein complex comprising a Cas endonuclease, a Cas endonuclease, a meganuclease, a TAL effector nuclease, an Argonaute, a Zinc Finger nuclease, and a fusion protein comprising a nuclease domain.

45. The method of claim 44, wherein the Cas endonuclease is selected from the group consisting of: Class 1, Class 2, Type I, Type II, Type III, Type IV, Type V, Type VI, Type I-A, Type I-B, Type I-C, Type I-U, Type I-D, Type I-E, Type I-F, Type III-A, Type III-B, Type III-C, Type III-D, Type II-A, Type II-B, Type II-C, Type V-A, Type V-B, Type V-C, Type V-D, Type V-E, Type V-U, Type V-U1, Type V-U2, Type V-U3, Type V-U4, Type VI-A, Type VI-C, Type VI-B, Type VI-B1, Type VI-B2, Cas9, Cpf1, a Cas endonuclease lacking endonuclease activity, and a functional fragment or functional variant of any of the preceding.

46. The method of claim 32, wherein the polynucleotide library generated in the fragmenting/shearing step comprises polynucleotide molecules between 100 and 1000 nucleotides in length.

47. The method of claim 32, wherein the qualitative characteristic is selected from the group consisting of: location of the double-strand break within the polynucleotide of (a), nature of the double-strand-break site, polynucleotide composition of the double-strand-break site, polynucleotide composition of the sequence flanking the 5' end of the double-strand-break site, and the polynucleotide composition of the sequence flanking the 3' end of the double-strand break site.

48. The method of claim 47, wherein any of the polynucleotide compositions comprise a polynucleotide of interest selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a noncoding regulatory element, a marker, a complex trait locus, a QTL, and a heterologous polynucleotide.

49. The method of claim 32, wherein the quantitative characteristic is the number of nucleotides comprising a polynucleotide of interest identified from a sequence adjacent to the double-strand-break site, wherein the polynucleotide of interest is selected from the group consisting of: a Protospacer Adjacent Motif (PAM) sequence, a double-strand-break-inducing agent recognition site, a guide polynucleotide binding site, a ribonucleoprotein binding site, a double-strand-break-inducing agent binding site, a double-strand-break-inducing agent cleavage site, a gene, a non-coding regulatory element, a marker, a complex trait locus, a QTL, and a heterologous polynucleotide.

50. The method of claim 32, wherein a characteristic of the double-strand-break-inducing agent is additionally determined.

51. The method of claim 50, wherein the characteristic of the double-strand-break-inducing agent is selected from the group consisting of: target recognition site sequence, off-target recognition site sequence, target binding site sequence, off-target binding site sequence, target cleavage site sequence, off-target cleavage site sequence, percent cleavage activity, cleavage efficacy, cleavage efficiency, cleavage specificity, nature of cleavage activity, and the relative amounts of components of the double-strand-break-inducing agent.

52. The method of claim 32, wherein the value of said characteristic is compared to the value of the same characteristic of, or produced by, a reference double-strand-break-inducing agent.

53. The method of claim 52, wherein said value is increased as compared to that of the reference double-strand-break-inducing agent.

54. The method of claim 52, wherein said value is decreased as compared to that of the reference double-strand-break-inducing agent.

55. The method of claim 52, wherein said value is used to optimize a characteristic of a double-strand-break-inducing agent functional association.

56. The method of claim 32, wherein the double-strand-break-inducing agent is a ribonucleoprotein complex comprising a Cas endonuclease, and the characteristic that is optimized is selected from the group consisting of: the ability of the double-strand-break-inducing agent to effect cleavage at a target site, and the relative amounts of components of the ribonucleoprotein complex.

57. The method of claim 32, wherein the cleavage site is a target cleavage site.

58. The method of claim 32, wherein the cleavage site is an off-target cleavage site.

59. The method of claim 32, wherein the double-strand-break-inducing agent of step (b) comprises a ribonucleoprotein comprising a Cas endonuclease and a guide ribonucleotide.

60. The method of claim 59, wherein the concentration of the ribonucleoprotein is at least 0.25 nM.

61. The method of claim 59, wherein the ratio of guide RNA to Cas endonuclease is 3:1.

62. The method of claim 32, wherein a plurality of double-strand-break-inducing agents are evaluated in parallel.

63. A method for characterizing a double-strand-break-inducing agent cleavage site of an isolated, purified polynucleotide, comprising:
(a) adding phosphatase to the isolated, purified polynucleotide, wherein the isolated, purified polynucleotide is of high molecular weight,
(b) contacting the phosphatase-treated polynucleotide from (a) with a double-strand-break-inducing agent to create a library of polynucleotides,
(c) adding an adenine to the 3' ends of the polynucleotides of the library,
(d) ligating an adapter to the polynucleotides of the library, wherein the adapter comprises a nucleotide that is complementary to a terminal unpaired nucleotide of the polynucleotides of (b) or (c), and
(e) sequencing said library of polynucleotides and identifying at least one double-strand-break site, and
(f) assessing at least one qualitative characteristic or quantitative characteristic of the double-strand-break site;
wherein the phosphatase addition results in an increased number of double-strand-break sequence reads compared to a control method not comprising the addition of phosphatase.

64. The method of claim 63, wherein the isolated, purified polynucleotide is greater than 50 kb.

* * * * *